(12) United States Patent
Kuroda et al.

(10) Patent No.: US 7,648,490 B2
(45) Date of Patent: Jan. 19, 2010

(54) SANITARY NAPKIN HAVING PLURALITIES OF PROJECTIONS AND ELASTIC MEMBERS

(75) Inventors: Kenichiro Kuroda, Mitoyo-gun (JP);
Wataru Yoshimasa, Mitoyo-gun (JP);
Toshiyuki Tanio, Mitoyo-gun (JP);
Shinobu Fujikawa, Mitoyo-gun (JP)

(73) Assignee: Uni-Charm Corporation, Ehime (JP)

( * ) Notice: Subject to any disclaimer, the term of this patent is extended or adjusted under 35 U.S.C. 154(b) by 100 days.

(21) Appl. No.: 11/288,840

(22) Filed: Nov. 28, 2005

(65) Prior Publication Data

US 2006/0142723 A1    Jun. 29, 2006

(30) Foreign Application Priority Data

Dec. 28, 2004   (JP)   ............... 2004-378874

(51) Int. Cl.
*A61F 13/20* (2006.01)
(52) U.S. Cl. ............... 604/385.01; 604/385.03; 604/385.04; 604/385.101; 604/385.201; 604/385.23; 604/385.27; 604/385.28
(58) Field of Classification Search ........... 604/385.17, 604/385.12, 385.01, 358, 385.03, 385.04, 604/385.101, 385.201, 385.23, 385.27, 385.28; D24/124
See application file for complete search history.

(56) References Cited

U.S. PATENT DOCUMENTS

| | | | |
|---|---|---|---|
| 4,770,657 A * | 9/1988 | Ellis et al. ............... | 604/385.31 |
| 5,624,423 A * | 4/1997 | Anjur et al. ............. | 604/385.21 |
| 6,191,340 B1 * | 2/2001 | Carlucci et al. ............. | 604/369 |
| 6,210,385 B1 * | 4/2001 | Mizutani ............... | 604/385.01 |
| 6,316,688 B1 * | 11/2001 | Hammons et al. .......... | 604/378 |
| 6,425,890 B1 * | 7/2002 | Samuelsson et al. ... | 604/385.71 |
| 6,500,159 B1 * | 12/2002 | Carvalho ............... | 604/385.01 |
| 6,617,490 B1 * | 9/2003 | Chen et al. .................. | 604/380 |
| 2001/0021834 A1 * | 9/2001 | Yoshimasa ............. | 604/385.01 |
| 2002/0068915 A1 * | 6/2002 | Drevik et al. .......... | 604/385.01 |
| 2003/0088222 A1 * | 5/2003 | Yoshimasa et al. .......... | 604/380 |
| 2005/0124951 A1 | 6/2005 | Kudo et al. | |

FOREIGN PATENT DOCUMENTS

| | | | |
|---|---|---|---|
| JP | 09-313529 A | | 12/1997 |
| JP | 11-042250 A | | 2/1999 |
| JP | 11-513921 A | | 11/1999 |
| JP | 2000-083994 A | | 3/2000 |
| JP | 2001-504727 A | | 4/2001 |
| JP | 2002-159534 | * | 6/2002 |

(Continued)

OTHER PUBLICATIONS

Office Action dated Sep. 28, 2007, issued in U.S. Appl. No. 11/123,608.

*Primary Examiner*—Tatyana Zalukaeva
*Assistant Examiner*—Ginger T Chapman
(74) *Attorney, Agent, or Firm*—Darby & Darby

(57) ABSTRACT

A sanitary napkin includes: a napkin body having a liquid-absorbent layer for absorbing and retaining liquid; and first and second projections each exerting an elastic contractive force between longitudinally opposing front and rear ends to concavely curve the body surface of the napkin body and raise itself from the body surface of the napkin body. The napkin body has an overlap region where the second projections lie on laterally opposite sides of the first projection.

11 Claims, 18 Drawing Sheets

FOREIGN PATENT DOCUMENTS

| | | |
|---|---|---|
| JP | 2002-301097 A | 10/2002 |
| JP | 2002-320638 A1 | 11/2002 |
| JP | 2003-093442 A | 4/2003 |
| JP | 2004-181085 A | 7/2004 |
| WO | WO-98/00085 A1 | 1/1998 |
| WO | WO-98/22060 A1 | 5/1998 |
| WO | WO-02/087483 A1 | 11/2002 |

* cited by examiner

SANITARY NAPKIN HAVING PLURALITIES OF PROJECTIONS AND ELASTIC MEMBERS

INCORPORATION BY REFERENCE

The present application claims priority under 35 U.S.C. §119 to Japanese Patent Application No. 2004-378874 filed on Dec. 28, 2004 in the Japanese language, which is hereby incorporated by reference in its entirety.

BACKGROUND OF THE INVENTION

1. Field of the Invention

The present invention relates to a sanitary napkin which can conform to the contours of the crotch of a woman so as to be effective in preventing gaps between the sanitary napkin and parts of the crotch and preventing leakage of menstrual blood.

2. Description of the Related Art

There have been known sanitary napkins with a napkin body containing a liquid-absorbent layer and a projection projecting from a body surface of the napkin body. The projection is constructed to exert a longitudinal elastic contractive force to concavely curve the body surface of the napkin body and raise itself from the body surface of the napkin body.

Japanese Unexamined Patent Application Publication No. H09-313529 discloses a sanitary napkin whose upper surface layer is centrally folded to form a jetty. This jetty has longitudinally-extending elastic members in its right and left side portions. Japanese Unexamined Patent Application Publication No. 2002-320638 discloses a sanitary napkin in which a T-section three-dimensional wall is formed of a liquid-permeable sheet and lies on the body surface of the napkin body. This three-dimensional wall has elastic members for exerting a longitudinal contractive force. In these Patent Publications, the body surface of the napkin body can be concavely curved by a longitudinal elastic contractive force of the elastic members. As a result, the jetty or three-dimensional wall, which extends along the longitudinal centerline, rises up from the body surface of the napkin body. Since the jetty or three-dimensional wall, which projects from the body surface of the napkin body, can easily come into contact with the vagina, menstrual blood discharged from the vagina can easily be collected by the jetty or three-dimensional wall.

Japanese Unexamined Patent Application Publication No. 2003-93442 discloses a diaper with three-dimensional guards extending longitudinally on right and left side portions. Each three-dimensional guard is provided with an elastic string adapted to exert a longitudinal elastic contractive force. Owing to the elastic contractive force of the elastic string, the body surface of the diaper body can be concavely curved, which results in rising of the three-dimensional guards from the body surface of the diaper body. The three-dimensional guards, which project from the right and left side portions of the diaper body, are brought into contact with the crotch of a wearer to prevent lateral leakage of urine and the like. In this Patent Publication, the bending stiffness of the diaper body is made higher in the front part than in the rear part so that the diaper body can easily be bent in the rear part of a relatively low bending stiffness.

Japanese Unexamined Patent Application Publication No. 2002-301097 discloses an absorbent article which has two types of elastic members and is applicable to disposable diapers, sanitary napkins, and incontinence pads. This absorbent article has three-dimensional gathers extending longitudinally on right and left side portions of the article body. The body surface of the article body can be concavely curved due to a longitudinal elastic contractive force exerted by the three-dimensional gathers. In a rear end portion of the article body, a fold is formed by embossing an absorbent core. This fold is provided with an elastic member so as to facilitate protuberance of the fold toward the body.

In the sanitary napkins disclosed in Patent Publication Nos. H09-313529 and 2002-320638, since the elastic members provided in the jetties or three-dimensional walls exert an elastic contractive force between front and rear ends of the napkin body, the napkin body is subjected to an almost uniform bending stress from the front end to the rear end. In the woman's crotch, however, the anteroposterior curvature generally varies such that the radius of curvature is relatively large across the vaginal opening, relatively small at a location spaced about 60 mm rearward from the center of the vaginal opening, and intermediate at a location spaced about 120 mm rearward from the center of the vaginal opening. Thus, the napkin body, which is subjected to an almost uniform bending stress between the front and rear ends, tends to leave a gap between the napkin body and a part of the wearer's body, which may cause leakage of menstrual blood and the like.

In the diaper disclosed in the Patent Publication No. 2003-93442, the curvature of the diaper body varies with location due to difference in stiffness between the front and rear parts of the diaper body. However, the front part of a relatively high bending stiffness tends to be difficult to bend in the front part of the crotch. As a result, there is a possibility that the front part of the diaper body will not snugly fit the wearer's body.

In the absorbent article disclosed in the Patent Publication No. 2002-301097, there are provided two types of elastic members: one being provided exclusively for raising the three-dimensional gathers; the other being provided in a different location from the former and exclusively for maintaining the shape of the fold. Here, since the curvature of the article body depends on the elastic members of the three-dimensional gathers, the article body cannot easily conform to the contours of the crotch.

SUMMARY OF THE INVENTION

The present invention has been developed to solve the problems in the prior art set forth above and has an object to provide a sanitary napkin whose napkin body can easily conform to the contours of the crotch of a woman.

According to the present invention, there is provided a sanitary napkin comprising:

a napkin body having a liquid-absorbent layer for absorbing and retaining liquid; and first and second projections each exerting an elastic contractive force between longitudinally opposing front and rear ends to concavely curve the body surface of the napkin body and raise itself from the body surface of the napkin body, wherein the napkin body has an overlap region where the second projections lie on laterally opposite sides of the first projection.

In the sanitary napkin according to the present invention, both the first and second projections exert an elastic contractive force on the overlap region. Accordingly, the bending stress acting on the napkin body varies with location, which results in that curvature is different for different regions of the napkin body.

According to one embodiment of the present invention, the first projection may extend on a longitudinal centerline of the napkin body, and the second projections may lie on laterally opposite sides of the longitudinal centerline. In this embodiment, the first projection is intended to face and fit against the intergluteal cleft, or the intergluteal cleft and the anus, or the vagina. On the other hand, the second projections are intended to serve as leakage preventing walls for preventing lateral leakage of liquid applied to the napkin body.

The first and second projections may each be comprised of a sheet allowed to rise from the body surface of the napkin body and an elastic member adapted to exert an elastic contractive force between the front and rear ends for raising the sheet.

Preferably, a midpoint between the front and rear ends of the first projection is located behind a midpoint between the front and rear ends of the second projection. For example, the front and rear ends of the first projection may be located behind the front and rear ends of the second projection, respectively. In this construction, preferably, the napkin body has front and rear regions on longitudinally opposite sides of the overlap region; front and rear ends of the front region are defined by the front end of the second projection and the front end of the first projection, respectively; front and rear ends of the rear region are defined by the rear end of the second projection and the rear end of the first projection, respectively; a bending stress which is exerted on the napkin body by the first and second projections is higher in the overlap region than in the front and rear regions. Moreover, the bending stress in the front region is preferably equal to or lower than the bending stress in the rear region. With this construction, the napkin body tends to have a relatively small radius of curvature in the overlap region, thereby easily conforming to the contours of the crotch of a woman. Also preferably, the napkin body has compression lines which extend longitudinally at least in the front region. With the compression lines, the front region of the napkin body can be made less flexible to have a relatively large radius of curvature.

Preferably, a midpoint between front and rear ends of the overlap region is located behind a vagina-facing reference line of the napkin body. More preferably, the front end of the first projection is not spaced more than 120 mm rearward from the vagina-facing reference line. With this construction, the napkin body tends to have a relatively small radius of curvature behind the vagina.

According to one embodiment of the present invention, the sanitary napkin may further comprise third projections which also exert an elastic contractive force between longitudinally opposing front and rear ends to concavely curve the body surface of the napkin body, wherein a midpoint between the front and rear ends of the first projection and a midpoint between the front and rear ends of the third projections are located behind a midpoint between the front and rear ends of the second projection. In the overlap region, preferably, not only the second projections but also the third projections lie on laterally opposite sides of the first projection. More preferably, the third projections are located between the first projection and the second projections.

According to the present invention, the bending stress acting on the napkin body varies with location. Therefore, the curvature of the napkin body may also vary with location so that the napkin body can conform to the contours of the crotch of a woman.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscuring of the present invention.

Figure 1:
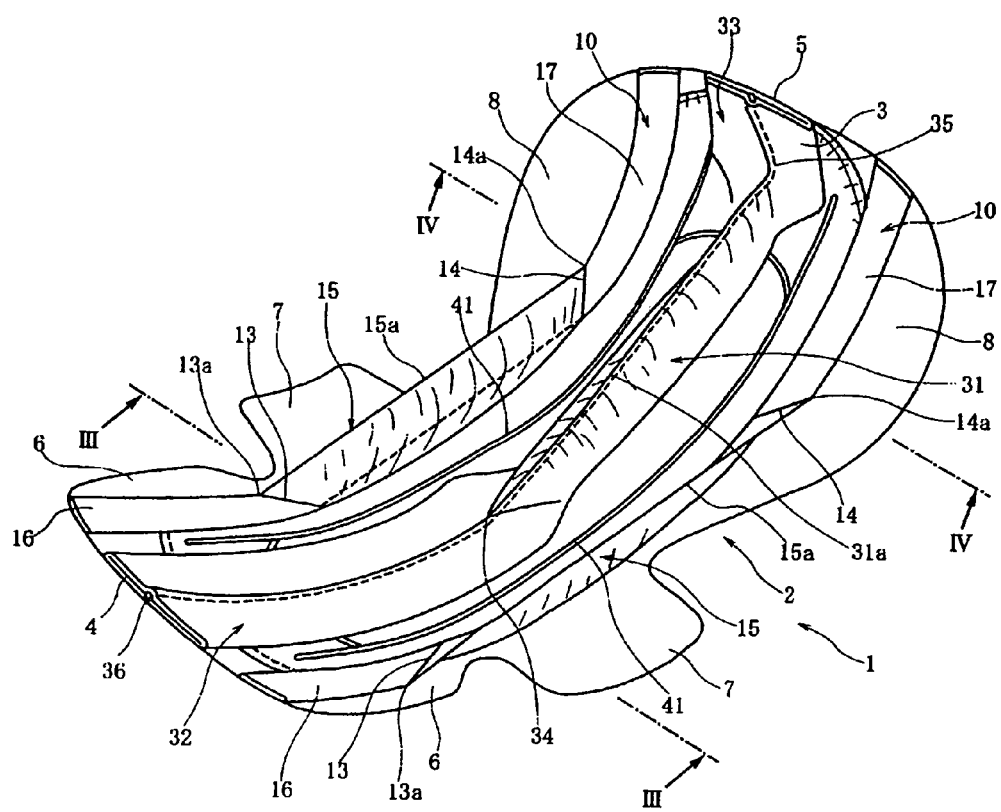
FIG. 1 is a perspective view of a sanitary napkin according to a first embodiment of the present invention in a natural state where no external force is exerted thereon.
Figure 2:
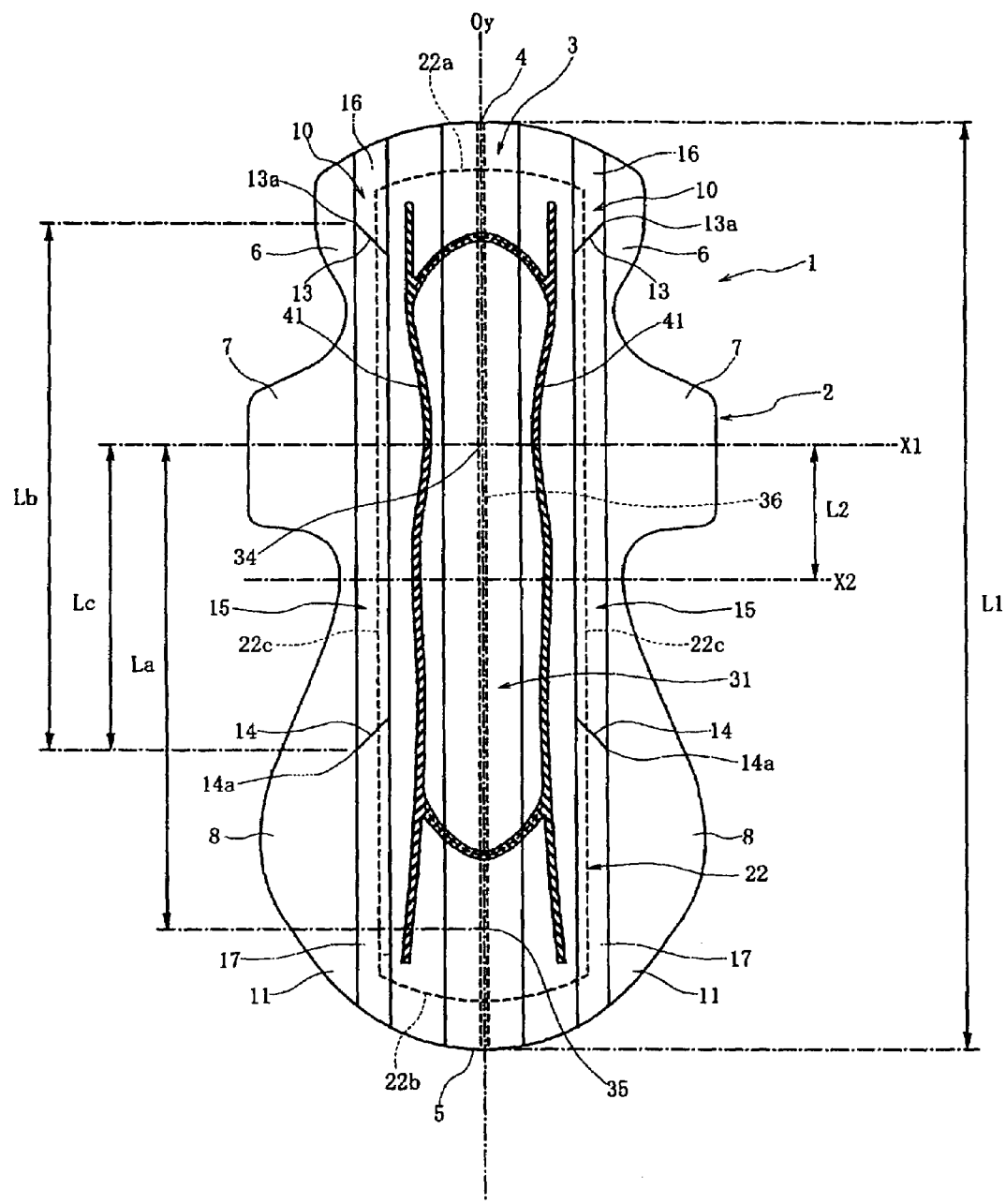
FIG. 2 is a plan view showing a body surface of a flattened sanitary napkin according to the first embodiment.
Figure 3:
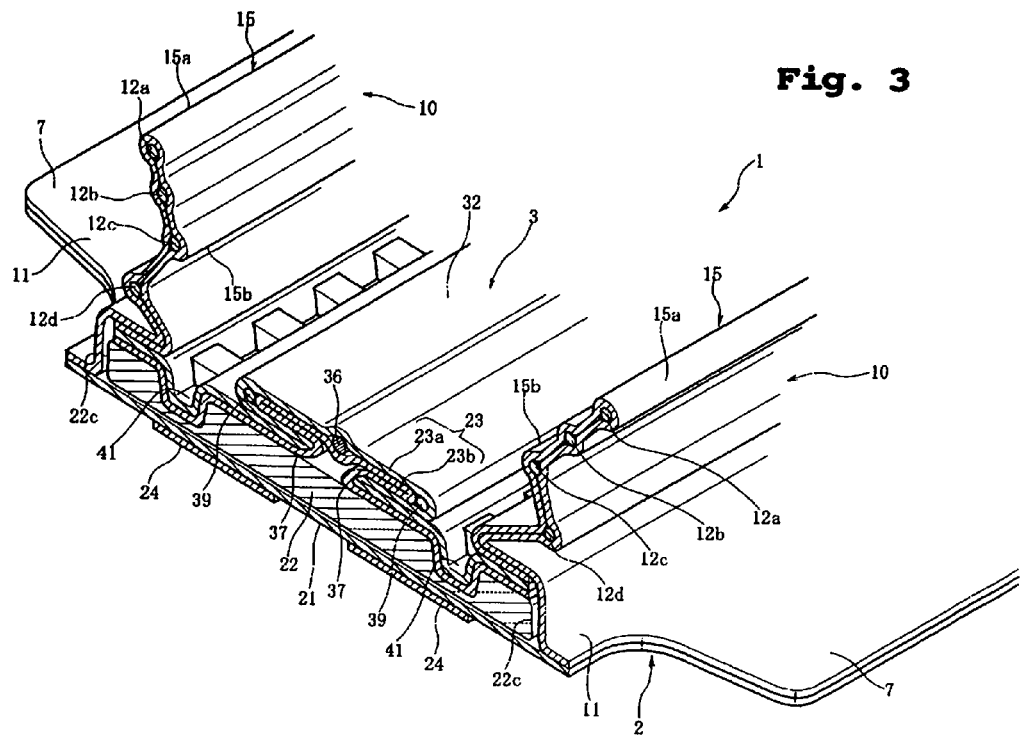
FIG. 3 is a sectional view taken along line III-III of FIG. 1.
Figure 4:
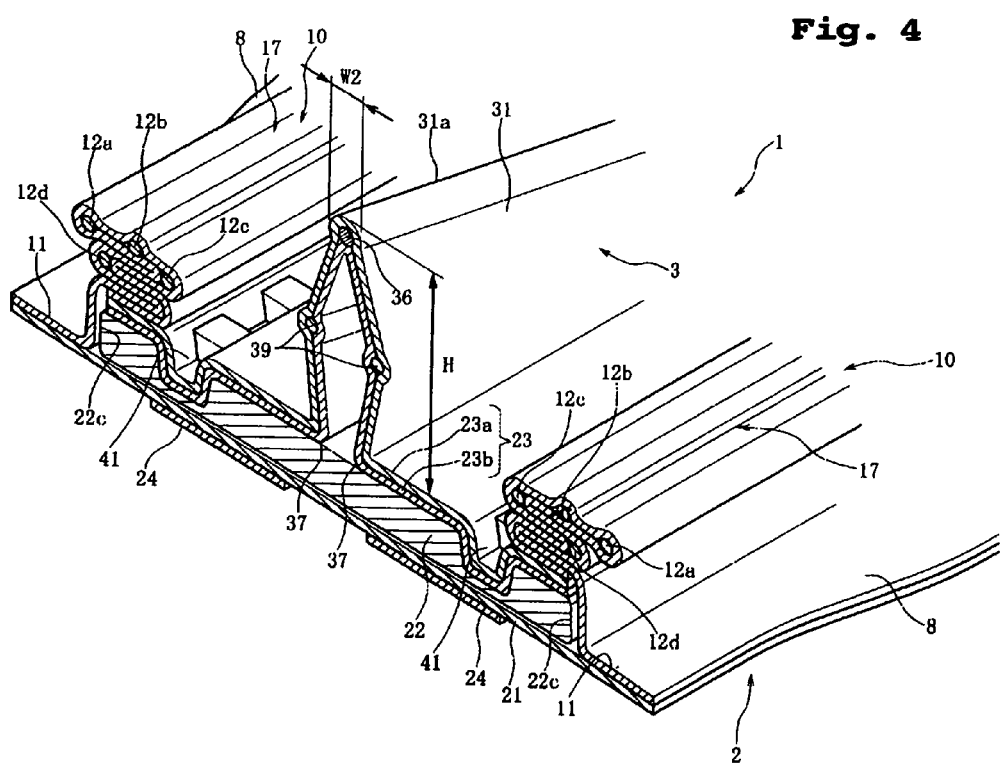
FIG. 4 is a sectional view taken along line IV-IV of FIG. 1.
Figure 5:
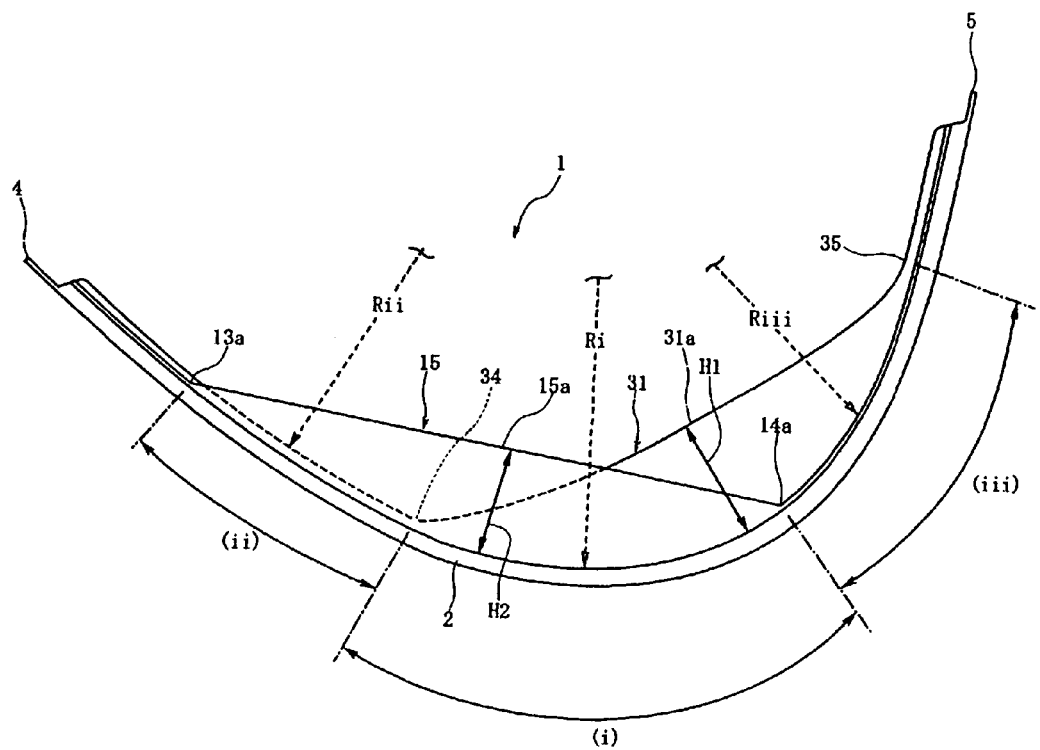
FIG. 5 is a side view of a sanitary napkin according to the first embodiment in a natural state where no external force is exerted thereon.
Figure 6:
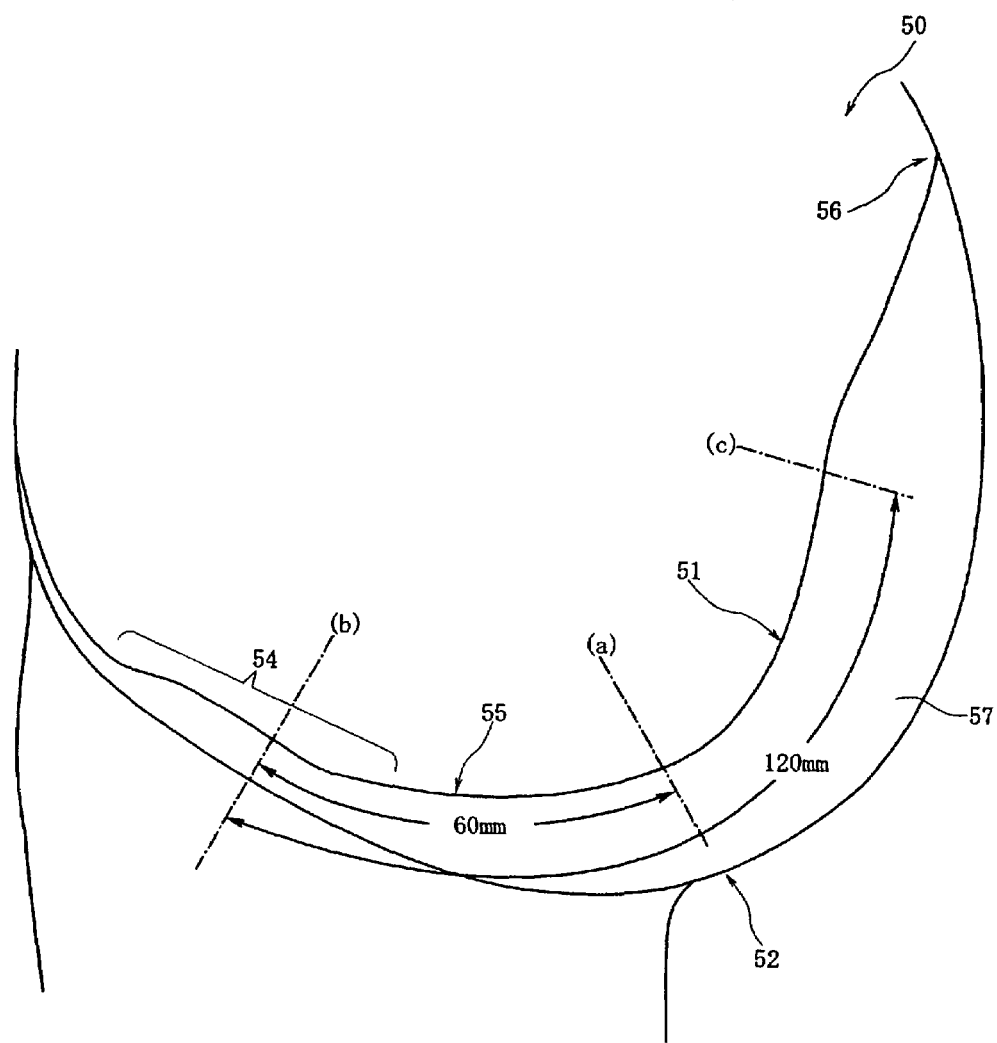
FIG. 6 is a sectional view showing the contours of the crotch of a woman.

FIG. 1 is a perspective view of a sanitary napkin 1 according to a first embodiment of the present invention in a natural state where no external force is exerted thereon. FIG. 2 is a plan view in which the sanitary napkin 1 is flattened. FIG. 3 is a sectional view taken along line III-III of FIG. 1, and FIG. 4 is a sectional view taken along line IV-IV of FIG. 1. FIG. 5 is a side view of the sanitary napkin 1 in a natural state where no external force is exerted thereon, and FIG. 6 is a sectional view showing the contours of the crotch of a woman.

It should be noted that the sanitary napkin, as well as its individual components, has two major surfaces: of which one surface intended to be worn toward the wearer's crotch is referred to as "body surface", while the other surface is referred to as "garment surface". In addition, the lengthwise direction of the sanitary napkin is referred to as "longitudinal direction", while the direction perpendicular to the longitudinal direction is referred to as "lateral direction". With respect to dimensions of the individual components, unless otherwise stated, a dimension measured in the longitudinal direction is referred to as "length", while a dimension measured in the lateral direction is referred to as "width".

The sanitary napkin 1 comprises a napkin body 2, a first surface element 3 disposed on the body surface of the napkin body 2 to form a first projection 31, and a pair of second surface elements 10, 10 disposed on the body surface of the napkin body 2 to form second projections 15, 15.

As shown in FIGS. 3 and 4, the napkin body 2 includes a liquid-blocking backsheet 21 on the garment surface side of the napkin body 2, a liquid-absorbent layer 22 disposed on the backsheet 21, and a liquid-permeable topsheet 23 covering the liquid-absorbent layer 22. The first surface element 3 is located on a longitudinal centerline Oy and includes a part of the topsheet 23.

As shown in FIG. 2, the napkin body 2 has arcuate front and rear edges 4, 5. The napkin body 2 is elongated to have a length L1 in the range of 280 to 450 mm. The liquid-absorbent layer 22 is also elongated to have arcuate front and rear edges 22a, 22b, which are spaced slightly inward from the front and rear edges 4, 5, respectively. Furthermore, the liquid-absorbent layer 22 has right and left side edges 22c, 22c, which extend linearly in parallel to the longitudinal centerline Oy.

On laterally opposite sides of the liquid-absorbent layer 22, the napkin body 2 has laterally projecting front flaps 6, 6, laterally projecting fold-back flaps 7, 7, and laterally projecting rear flaps 8, 8 in order from front to rear.

On the body surface side of the napkin body 2, furthermore, liquid-blocking or water-repellent side sheets 11, 11 lie opposite one another. Outside the side edges 22c, 22c of the liquid-absorbent layer 22, the side sheets 11, 11 are bonded to the backsheet 21 through a hot-melt type adhesive. The side sheets 11, 11 are also bonded to the body surface of the topsheet 23 above the side portions of the liquid-absorbent layer 22, as shown in FIGS. 3 and 4. Thus, the side sheets 11, 11 provide the second surface elements 10, 10.

The second surface elements 10, 10 are spaced a uniform distance laterally from the longitudinal centerline Oy to define therebetween a main liquid-absorbent region where the topsheet 23 is exposed externally.

X1 shown in FIG. 2 represents a vagina-facing reference line, and this vagina-facing reference line X1 is spaced 100 to 200 mm rearward from the front edge 4 of the napkin body 2.

The vagina-facing reference line X1 as used herein is a target position with which the center of the vaginal opening is to almost coincide when wearing the sanitary napkin 1. Leading to this target is through the contour of the sanitary napkin as viewed from the body surface side or the whole design including the arrangement of compression lines on the body surface. Particularly when the fold-back flaps 7, 7 and compression lines 41 are provided as in the embodiment shown in FIG. 2, the target usually coincides with the longitudinal centers of the fold-back flaps 7, 7 or the position where the lateral distance between the compression lines 41 is minimum.

In the present embodiment, the line passing through the position where the lateral distance between the compression lines 41 is minimum is taken as the vagina-facing reference line X1. The vagina-facing reference line X1 almost coincides with the longitudinal centers of the fold-back flaps 7, 7.

X2 shown in FIG. 2 represents an anus-facing reference line, and this anus-facing reference line X2 is intended to face the anus when the vagina-facing reference line X1 coincides with the center of the vaginal opening. The anus-facing reference line X2 is usually spaced a distance L2 of 30 to 70 mm, which varies depending on the wearer's body, rearward from the vagina-facing reference line X1.

The backsheet 21 may be a film, for example, a polyethylene resin film having a basis weight of about 23 g/m$^2$, and is preferably permeable to moisture. The liquid-absorbent layer 22 may be a mixture of fluff pulp and superabsorbent polymer (SAP) wrapped in a hydrophilic tissue, wherein the fluff pulp has a weight of about 400 g/m$^2$. The side sheet 11 may be a spunbonded nonwoven fabric of polyethylene/polypropylene sheath/core bicomponent fibers.

The topsheet 23 may be a laminate of first and second liquid-permeable sheets 23a, 23b. The first and second liquid-permeable sheets 23a, 23b may each be a through-air bonded nonwoven fabric having a basis weight of about 25 g/m$^2$. The through-air bonded nonwoven fabric may be made of polyethylene/polyethylene terephthalate sheath/core bicomponent fibers with an inorganic filler such as titanium oxide mixed into the core of polyethylene terephthalate. Preferably, 80% of the sheath/core bicomponent fibers are made hydrophilic by coating of a hydrophilic lubricant; 20% of the sheath/core bicomponent fibers are made water-repellent by coating of a water-repellent lubricant.

In order to prevent separation, the first and second liquid-permeable sheets 23a, 23b may be bonded to each other through a hot-melt type adhesive which is applied to such an extent as not to interfere with liquid passage (e.g., in an amount of 2 g/m$^2$).

The liquid-permeable sheet for the topsheet 23 is not limited to the above-mentioned through-air bonded nonwoven fabric. For example, there may be used a point-bonded, spunlaced, or spunbonded nonwoven fabric. Here, the fiber density is preferably 0.12 g/cm$^3$ or less so as to improve liquid-permeability. Alternatively, there may be used a resin film formed with a large number of apertures for liquid passage. If desired, the apertured resin film may be used as the first liquid-permeable sheet 23a, while the nonwoven fabric such as through-air bonded may be used as the second liquid-permeable sheet 23b. The topsheet 23 may be embossed in a dot pattern or corrugated.

As shown in FIGS. 3 and 4, boundaries 37, 37 extend in parallel to the longitudinal direction at locations spaced an equal distance laterally from the longitudinal centerline Oy. Outside the boundaries 37, 37, the topsheet 23 is bonded to the body surface of the liquid-absorbent layer 22. Between the boundaries 37, 37, on the other hand, the topsheet 23 remains unbonded to the body surface of the liquid-absorbent layer 22, providing the first surface element 3.

The first surface element 3 includes an elastic member 36 which is disposed between the first and second liquid-permeable sheets 23a, 23b and bonded thereto through a hot-melt type adhesive. In FIG. 2, the elastic member 36 extends on the longitudinal centerline Oy. Between front and rear ends 34, 35 of the first projection 31, the elastic member 36 is allowed to move away from the body surface of the napkin body 2. In other words, the elastic member 36 is secured on the body surface of the napkin body 2 forward of the front end 34 of the first projection 31 and behind the rear end 35 of the first projection 31.

Between the front end 34 of the first projection 31 and the front edge 4 of the napkin body 2, a portion of the topsheet 23 extending between the boundaries 37, 37 is folded flat to provide a front flat portion 32, as shown in FIG. 3. The front flat portion 32 is secured on the body surface of the napkin body 2. Between the rear end 35 of the first projection 31 and the rear edge 5 of the napkin body 2, a portion of the topsheet 23 is also folded flat to provide a rear flat portion 33. The rear flap portion 33 is secured on the body surface of the napkin body 2.

The elastic member 36 is adapted to exert an elastic contractive force. Thus, the front and rear ends 34, 35 approach each other under elastic tension to concavely curve the body surface of the napkin body 2, as shown in FIG. 1. Between the front and rear ends 34, 35, more specifically, the elastic member 36 moves away from the body surface of the napkin body 2 to elevate the topsheet 23 (the first and second liquid-permeable sheets 23a, 23b) with its base ends at the boundaries 37, 37. Thus, the first surface element 3 provides the first projection 31 between the front and rear ends 34, 35. As shown in FIG. 4, the first projection 31 is hollow. The elastic member 36 is contained in an apex 31a of the first projection 31. The apex 31a extends on the longitudinal centerline Oy.

In the first surface element 3, furthermore, a pair of side elastic members 39, 39 are bonded between the first and second liquid-permeable sheets 23a, 23b. As shown in FIG. 3, the side elastic members 39, 39 are located at both side edges of the individual flat portions 32, 33.

In the front and rear flat portions 32, 33, front and rear portions of each side elastic member 39 are secured to the napkin body 2. Here, an intermediate portion of each side elastic member 39 which is allowed to move away from the napkin body 2 has a front connection point (or front footpoint) behind the front end 34 and a rear connection point (or rear footpoint) forward of the rear end 35. As shown in FIG. 4, the side elastic members 39, 39, which are moved away from the body surface of the napkin body 2, are laterally spaced from each other and located closer to the body surface of the napkin body 2 than the elastic member 36.

The elastic member 36 and the side elastic members 39 may be polyurethane elastic filaments. The elastic tension exerted by the elastic member 36 between the front and rear ends 34, 35 is preferably lower than the elastic tension exerted by each side elastic member 39 between the front and rear connection points. The elastic member 36 may have a fineness in the range of 240 to 10000 dtex, preferably in the range of 1800 to 8000 dtex. The side elastic member 39 may have a fineness in the range of 120 to 6000 dtex, preferably in the range of 240 to 4000 dtex. If desired, the elastic member 36 and the side elastic member 39 may be made by bundling or twisting a plurality of thin elastic filaments. In this case, the respective elastic members may be prepared such that the total fineness of the thin elastic filaments falls within the above range.

Alternatively, the elastic member 36 and the side elastic member 39 may be rubber threads, such as of natural rubber or synthetic rubber, or thin strips cut from a stretchable film, a stretchable nonwoven fabric, or a stretchable resin foam such as urethane foam. The elastic member 36 and the side elastic member 39 are bonded between the first and second liquid-permeable sheets 23a, 23b while being stretched at least 1.2 times, preferably at least 1.5 times the original length.

Above the laterally opposing side portions of the liquid-absorbent layer 22, as shown in FIGS. 3 and 4, the side sheets 11, 11 are folded back to provide the second surface elements 10, 10. In each second surface element 10, four elastic members 12a, 12b, 12c, 12d are disposed between opposing faces of the folded side sheet 11 and bonded thereto through a hot-melt type adhesive.

As shown in FIG. 2, the second surface element 10 has a front join line 13 which extends obliquely in the front part of the napkin body 2. Between the front join line 13 and the front edge 4, there is defined a front join portion 16 where the side sheet 11 is folded flat and bonded on the body surface of the napkin body 2. The second surface element 10 also has a rear join line 14 which extends obliquely in the rear part of the napkin body 2. Between the rear join line 14 and the rear edge 5, there is defined a rear join portion 17 where the side sheet 11 is folded flat and bonded on the body surface of the napkin body 2.

FIG. 4 shows the rear join portion 17. In the rear join portion 17, the side sheet 11 is folded at the elastic members 12c, 12d and secured on the body surface of the napkin body 2 with the elastic member 12a directed laterally outward. The side sheet 11 is also folded and secured in the front join portion 16.

The elastic members 12a-12d are adapted to exert an elastic contractive force between a front end 13a which is one end of the front join line 13 and a rear end 14a which is one end of the rear join line 14. Thus, a bending stress acts on the napkin body 2 to draw the front and rear ends 13a, 14a closer to each other and concavely curve the body surface of the napkin body 2. Between the front and rear ends 13a, 14a, more specifically, the elastic members 12a-12d move away from the body surface of the napkin body 2 to elevate the side sheet 11, thereby providing the second projection 15.

As shown in FIG. 3, the second projection 15 is a leakage preventing wall of a modified Z-shaped cross section, wherein an apex 15a contains the elastic member 12a and a crease 15b contains the elastic member 12c.

For the elastic members 12a-12d, there may be used materials similar to those mentioned with reference to the elastic member 36 and the side elastic member 39. The elastic tension exerted by the individual elastic members 12a-12d is preferably lower than the elastic tension exerted by the elastic member 36 of the first projection 31. For example, the elastic members 12a-12d may be polyurethane elastic filaments with a fineness in the range of 120 to 6000 dtex, preferably in the range of 240 to 4000 dtex. The elastic members 12a-12d are bonded to the side sheet 11 while being stretched at least 1.2 times, preferably at least 1.5 times the original length between the front and rear ends 13a, 14a.

As shown in FIGS. 1 and 2, the front end 34 of the first projection 31 is located on or near the vagina-facing reference line X1 of the napkin body 2. On the other hand, the rear end 35 is spaced about 120 to 250 mm rearward from the vagina-facing reference line X1. When a woman wears the sanitary napkin 1, the front end 34 faces the vaginal opening or its vicinity while the rear end 35 faces the coccyx or its vicinity. Thus, the first projection 31 faces the vaginal opening, the anus and the intergluteal cleft behind the anus.

The front ends 13a of the second projections 15 are located forward of the vagina-facing reference line X1 and the front end 34 of the first projection 31. On the other hand, the rear ends 14a of the second projections 15 are located behind the anus-facing reference line X2 and forward of the rear end 35 of the first projection 31.

When the backsheet 21 of the sanitary napkin 2 is flattened, as shown in FIG. 2, the length La of the first projection 31 between the front and rear ends 34, 35 may be, for example, 190 mm. Preferably, the length La is in the range of 50 to 250 mm. On the other hand, the length Lb of the individual second projections 15 between the front and rear ends 13a, 14a may be, for example, 200 mm. Preferably, the length Lb is in the range of 50 to 250 mm. Here, the overlap between the length La and the length Lb is indicated by Lc. In the region of the overlap length Lc, the second projections 15 lie on laterally opposite sides of the first projection 31. In other words, the first projection 31 and the second projections 15 lie side-by-side in the region of the overlap length Lc. Hereinbelow, the region of the overlap length Lc is called "overlap region".

The midpoint between the front and rear ends 34, 35 of the first projection 31 is located behind the anus-facing reference line X2. The midpoint between the front and rear ends 13a, 14a of the second projection 15 is located on the vagina-facing reference line X1 or between the vagina-facing reference line X1 and the anus-facing reference line X2. Here, the midpoint between the front and rear ends 34, 35 of the first projection 31 is located behind the midpoint between the front and rear ends 13a, 14a of the second projection 15.

The force exerted by the elastic members 36, 39 of the first projection 31 to draw the front and rear ends 34, 35 closer to each other (i.e., the elastic contractive force of the first projection 31) may be 0.5 to 6 N. On the other hand, the force exerted by the elastic members 12a-12d of each second projection 15 to draw the front and rear ends 13a, 14a closer to each other (i.e., the elastic contractive force of each second projection 15) may be 0.15 to 2 N. The total elastic contractive force of the two second projections 15 may be 0.3 to 4 N and is preferably smaller than the elastic contractive force of the first projection 31.

With this construction, the body surface of the napkin body 2 can be appropriately concavely curved by the first and second projections 31, 15.

In FIG. 5, (i) indicates the overlap region where the second projections 15 lie on laterally opposite sides of the first projection 31. Moreover, (ii) indicates a front region which is defined between the front end 34 of the first projection 31 and the front ends 13a of the second projections 15, and (iii) indicates a rear region which is defined between the rear end 35 of the first projection 31 and the rear ends 14a of the second projections 15. The force exerted on the napkin body 2 to cause curvature may be different for different regions such that the front region (ii)<the rear region (iii)<the overlap region (i). The bending stress acting on the napkin body 2 may also be different for different regions such that the front region (ii)<the rear region (iii)<the overlap region (i).

When the sanitary napkin 1 is in a natural state where no external force is exerted thereon, as shown in FIG. 5, therefore, the average radius of curvature of the body surface of the napkin body 2 may be different for different regions such that the average radius of curvature (Rii) in the front region>the average radius of curvature (Riii) in the rear region>the average radius of curvature (Ri) in the overlap region. In an alternative, the napkin body 2 may satisfy the above inequality when the sanitary napkin 1 is adhered to an inner side of an undergarment and put on the wearer's body.

When the napkin body 2 is flattened, as shown in FIG. 2, the length Lc of the overlap region (i) is preferably in the range of 15 to 200 mm, more preferably equal to or greater than 30 mm, so as to satisfy the above inequality.

FIG. 6 is a sectional view showing the contours of the crotch of a woman who stands 168 cm tall, weights 56 kg, and has a BMI (body mass index) of 19.8. Here, the BMI is a dimensionless value obtained by weight(kg)/height(m)$^2$.

In FIG. 6, an inner curve 51 shows the sectional profile along the bottom of an intergluteal cleft 57 and an outer curve 52 shows the profile of one buttock. The vagina, anus, and coccyx lie on the inner curve 51 and are indicated by 54, 55, and 56, respectively. The vagina 54 refers to an area including the labia majora.

When a location spaced 60 mm rearward from the center of the vaginal opening (b) along the inner curve 51 is indicated by (a) and a location spaced 120 mm rearward from the center of the vaginal opening (b) along the inner curve 51 is indicated by (c), as shown in FIG. 6, the radius of curvature varies such that the location (a)<the location (c)<the center of the vaginal opening (b) for both the inner curve 51 and the outer curve 52.

Thus, when the overlap region (i) faces the area including the location (a), the front region (ii) faces the area including the center of the vaginal opening (b), and the rear region (iii) faces the area including the location (c), the sanitary napkin 1, which is curved as shown in FIG. 5, can easily conform to the contours of the woman's crotch.

In order that the sanitary napkin 1 can easily fit the woman's crotch shown in FIG. 6, it is preferred that the overlap region (i) includes a location spaced 60 mm rearward from the vagina-facing reference line X1 shown in FIG. 2 or at least a part of the overlap region (i) lies between a location spaced at least 40 mm rearward from the vagina-facing reference line X1 and a location spaced 120 mm rearward from the vagina-facing reference line X1. That is, it is preferred that the front end 34 of the first projection 31 is not spaced more than 120 mm rearward from the vagina-facing reference line X1, the rear ends 14a of the second projections 15 are spaced more than 40 mm rearward from the vagina-facing reference line X1, and the length Lc of the overlap region (i) is equal to or greater than 15 mm, preferably equal to or greater than 30 mm.

The maximum height H1 of the first projection 31, which is measured from the body surface of the napkin body 2 to the apex 31a (see FIG. 5), is preferably in the range of 10 to 60 mm. Within this range, the first projection 31 can easily fit in the intergluteal cleft 57 shown in FIG. 6. If the width W2 of the apex 31a of the first projection 31 (the width of the portion containing the elastic member 36) shown in FIG. 4 is in the range of 1 to 3 mm, the apex 31a of the first projection 31 can easily find its way into the intergluteal cleft 57.

On the other hand, the maximum height H2 of the second projection 15, which is measured from the body surface of the napkin body 2 to the apex 15a (see FIG. 5), is preferably in the range of about 5 to 50 mm. Within this range, the apexes 15a of the second projections 15 can easily be kept in contact with the wearer's skin on both sides of the vagina 54 to effectively prevent lateral leakage of menstrual blood.

On the body surface of the napkin body 2, as shown in FIGS. 1 to 4, there are provided compression lines 41. The compression lines 41 are formed by pressing and heating the topsheet 23 and the liquid-absorbent layer 22 at the same time. The compression lines 41 extend continuously from forward of the front ends 13a of the second projections 15 to behind the rear end 35 of the first projection 31. In the compression lines 41, portions where the liquid-absorbent layer 22 is compressed to have a high density alternate longitudinally with portions where the liquid-absorbent layer 22 is compressed to have a lower density than the high-density portions.

The compression lines 41 function as a stiffening element. With the compression lines 41, the napkin body 2 can be stiffened to resist the elastic contractive force exerted by the elastic members 36, 39, 12a-12d. Although the compression lines 41 are not necessarily required to extend as shown in FIG. 2, it is preferred that the compression lines 41 are arranged at least in the front region (ii). The average radius of curvature (Rii) in the front region (ii) can easily be made relatively large by arranging the compression lines 41 in the front region (ii).

As shown in FIGS. 3 and 4, the napkin body 2 has pressure-sensitive adhesive layers 24 on the garment surface of the backsheet 21 for adhesion to an undergarment. The pressure-sensitive adhesive layers 24 extend parallel to and on both sides of the longitudinal centerline Oy. Although omitted in the drawings, it should be noted that the fold-back flaps 7, 7 and the rear flaps 8, 8 also have pressure-sensitive adhesive layers on the garment surface of the backsheet 21.

When using the sanitary napkin 1, the pressure-sensitive adhesive layers 24 on the garment surface of the napkin body 2 are adhered to the inner side of the undergarment. Then, the fold-back flaps 7, 7 are folded back upon the outer side of the undergarment along two side edges of a crotch part of the undergarment and then the pressure-sensitive adhesive layers on the garment surfaces of the fold-back flaps 7, 7 are adhered to the outer side of the crotch part. In addition, the pressure-sensitive adhesive layers on the garment surfaces of the rear flaps 8, 8 are adhered to the inner side of the undergarment at a lower part of a back body.

When the sanitary napkin 1 is adhered to the undergarment by a user, the vagina-facing reference line X1 serves as a target for positioning so that it can be worn with the vagina-facing reference line X1 almost coinciding with the longitudinal center of the vaginal opening. When in a natural state where no external force is exerted thereon or put on the wearer's body together with the undergarment, the sanitary napkin 1 tends to have a small average radius of curvature (Ri) in the overlap region (i) located behind the vagina-facing reference line X1, as shown in FIG. 5.

Thus, the napkin body 2 can easily conform to different curvatures of the woman's crotch shown in FIG. 6. In more detail, the front region (ii) with a relatively large radius of curvature faces the vagina and its vicinity so that the front flat portion 32 of the first surface element 3 and the front part of the first projection 31 can face the vagina. In addition, the second projections 15 rise up on both sides of the vagina so as to be in stable contact with the crotch. Furthermore, the overlap region (i) faces the wearer's body at a sharply curved location behind the anus, and the rear region (iii) faces the wearer's body further behind. Thus, the first projection 31 fits against the anus and the intergluteal cleft 57.

Menstrual blood discharged from the vaginal opening passes through spaces between fibers of the liquid-permeable sheets 23a, 23b under force of gravity and is quickly absorbed and retained due to hydrophilicity of the underlying liquid-absorbent layer 22. Since the first projection 31 can easily fit in the intergluteal cleft and the second projections 15 can act as leakage preventing walls, menstrual blood can easily be absorbed by the liquid-absorbent layer 22, preventing lateral or rearward leakage.

Hereinbelow, other embodiments of the sanitary napkin according to the present invention will be described.

Figure 7:
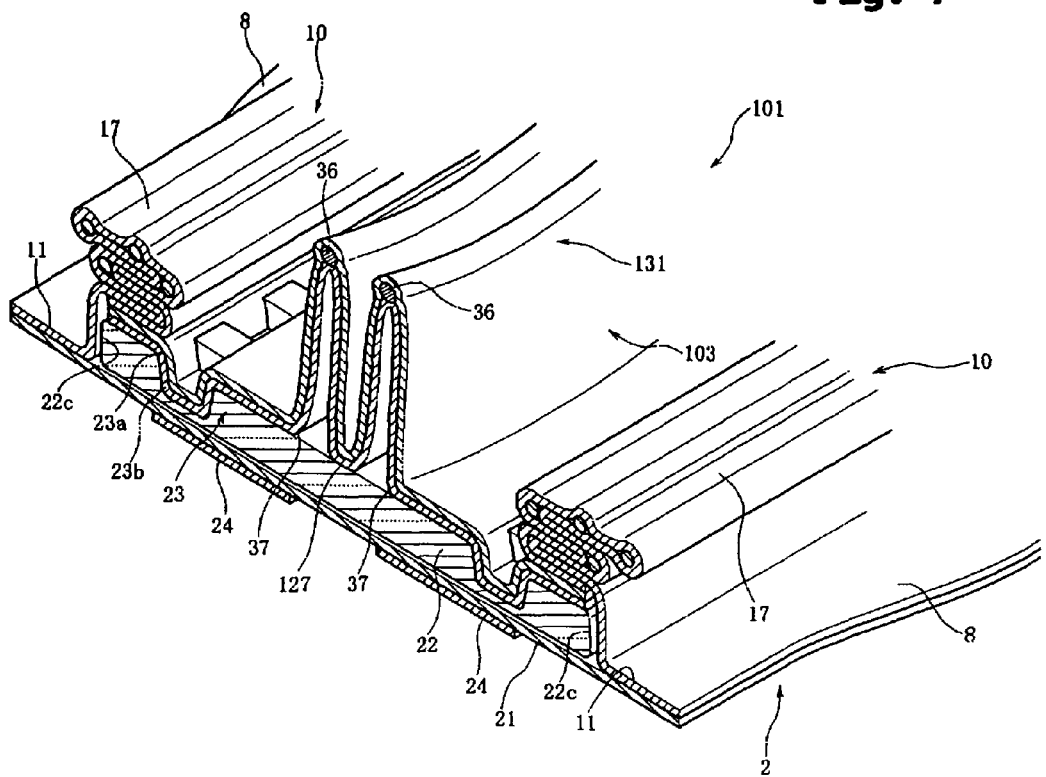
FIG. 7 is a sectional view showing a sanitary napkin according to a second embodiment of the present invention.

FIG. 7 is a sectional view corresponding to FIG. 4, showing a sanitary napkin 101 according to a second embodiment of the present invention.

In the sanitary napkin 101 according to the second embodiment, the napkin body 2 has the same construction as that of the first embodiment, but a first surface element 103 has two elastic members 36, 36 bonded between the first and second liquid-permeable sheets 23a, 23b. Then, the topsheet 23 is partly bonded to the body surface of the liquid-absorbent layer 22 at a location midway between the elastic members 36, 36.

Between the front end 34 and the rear end 35, therefore, two first projections 131 project from the body surface of the napkin body 2. On the other hand, the second surface elements 10 and the second projections 15 have the same constructions as those of the first embodiment.

Figure 8:
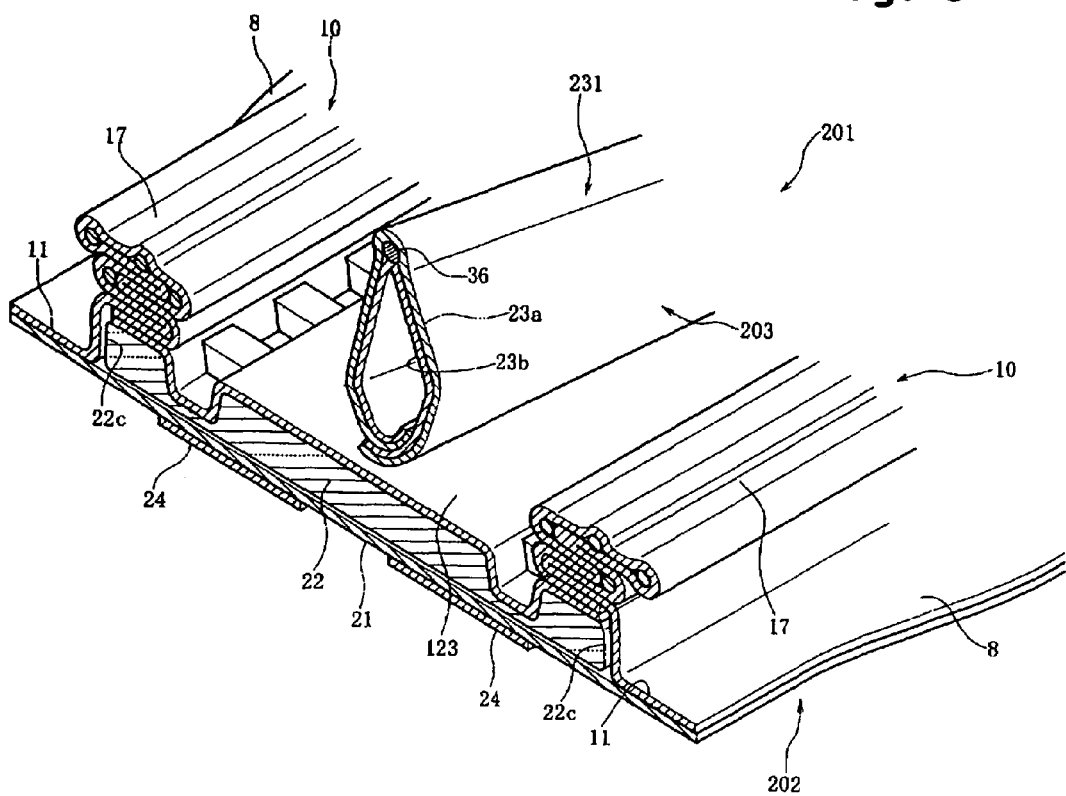
FIG. 8 is a sectional view showing a sanitary napkin according to a third embodiment of the present invention.

FIG. 8 is a sectional view corresponding to FIG. 4, showing a sanitary napkin 201 according to a third embodiment of the present invention.

In the sanitary napkin 201 according to the third embodiment, a first surface element 203 provides a first projection 231, at least a part of which is separated from the body surface of the napkin body 2 between the front end 34 and the rear end 35 so as to be able to move laterally above the napkin body 2.

In the first projection 231, the elastic member 36, which lies on the longitudinal centerline Oy, is interposed and bonded between the first and second liquid-permeable sheets 23a, 23b. The first projection 231 is of a hollow tubular construction with the opposite edges of the laminated liquid-permeable sheets 23a, 23b bonded to each other.

In the napkin body 202, the body surface of the liquid-absorbent layer 22 is covered with a liquid-permeable topsheet 123. The topsheet 123 may be made of the same material as used for the first and second liquid-permeable sheets 23a, 23b.

Forward of the front end 34 and behind the rear end 35, the first and second liquid-permeable sheets 23a, 23b are folded flat to provide the front flat portion 32 and the rear flat portion 33 which are similar to those of the first embodiment.

In the sanitary napkin 201 according to the third embodiment, even when the napkin body 202, which is adhered to the undergarment, is moved laterally by slippage of the undergarment, a fit of the first projection 231 in the intergluteal cleft can easily be maintained.

Figure 9:
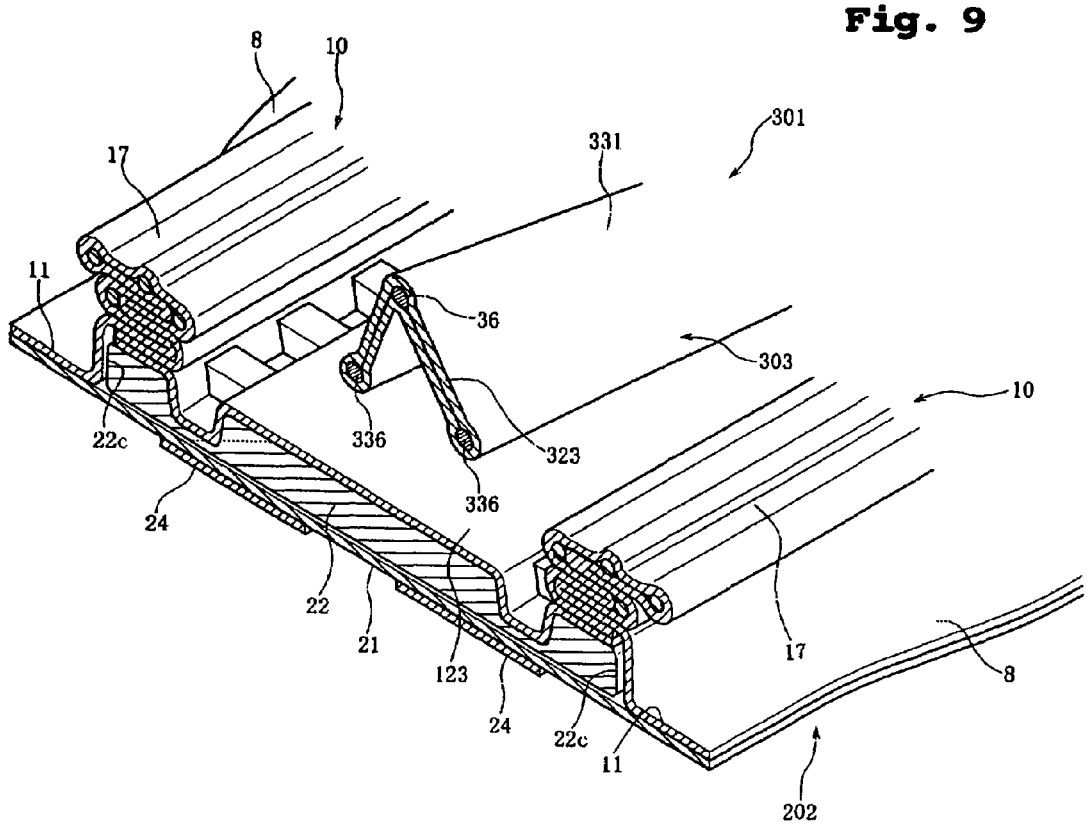
FIG. 9 is a sectional view showing a sanitary napkin according to a fourth embodiment of the present invention.

FIG. 9 shows a sanitary napkin 301 according to a fourth embodiment of the present invention.

In the sanitary napkin 301, the napkin body 202 has the same construction as that of the third embodiment shown in FIG. 8. Also in the fourth embodiment, a first surface element 303 provides a first projection 331, at least a part of which is separated from the body surface of the napkin body 202 between the front end 34 and the rear end 35 so as to be able to move laterally above the napkin body 202.

The first projection 331 is formed by folding a liquid-permeable sheet 323 to have an inverted V-shaped cross section. The elastic member 36, which lies on the longitudinal centerline Oy, is interposed and bonded between opposing faces of the liquid-permeable sheet 323. Moreover, side elastic members 336, 336 which are spaced an equal distance on both sides of the elastic member 36 are also interposed and bonded between opposing faces of the liquid-permeable sheet 323.

Figure 10:
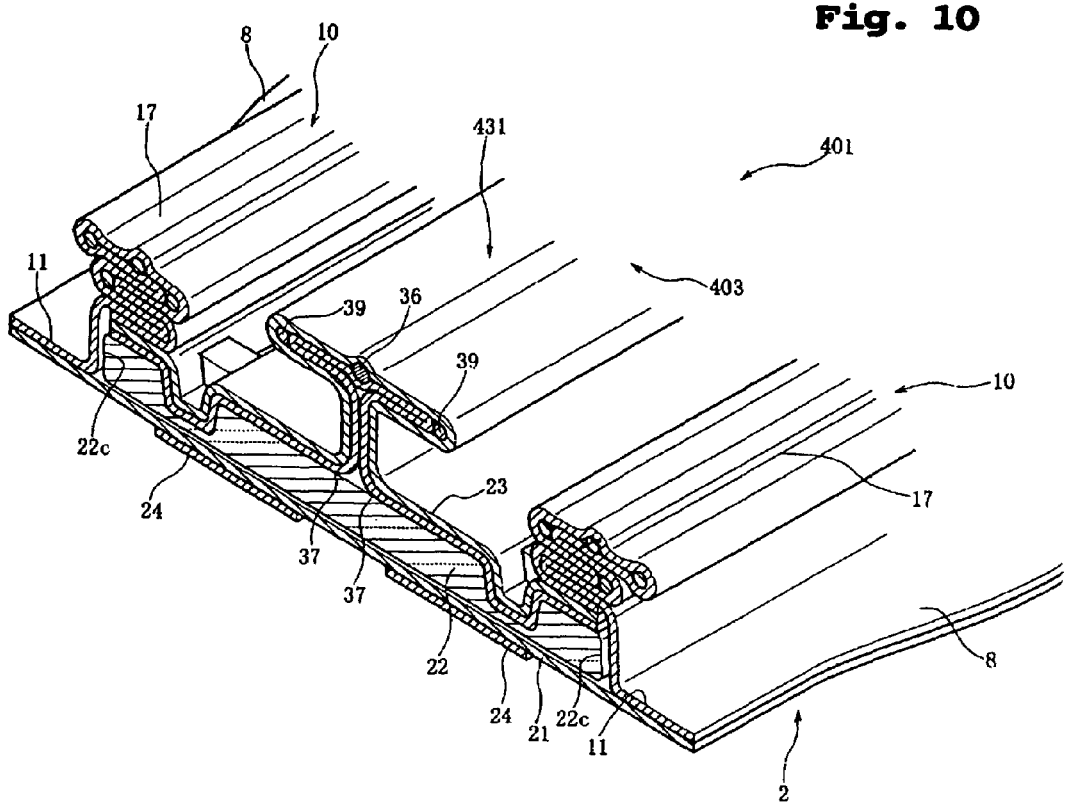
FIG. 10 is a sectional view showing a sanitary napkin according to a fifth embodiment of the present invention.

FIG. 10 shows a sanitary napkin 401 according to a fifth embodiment of the present invention.

In the sanitary napkin 401, the napkin body 2 has the same construction as that of the first embodiment. A first projection 431 of a first surface element 403 is formed by folding the topsheet 23 to have a T-shaped cross section.

Figure 11A:
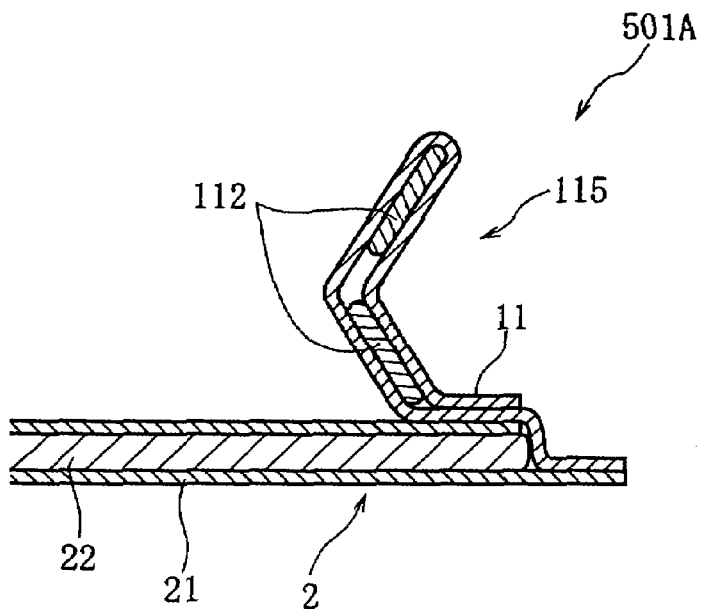
FIGS. 11(A) and 11(B) are partial sectional views showing modifications of a second projection.
Figure 11B:
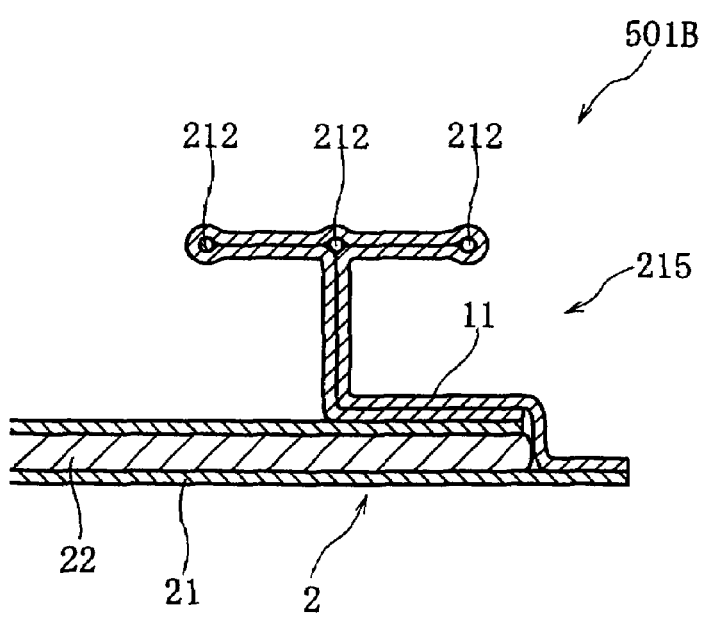

FIGS. 11(A) and 11(B) show other embodiments of the second projection.

FIG. 11(A) shows a sanitary napkin 501A, in which sheet-like elastic members 112 are disposed between opposing faces of the side sheet 11 to provide a second projection 115. The front and rear ends of the second projection 115 are drawn closer to each other by the sheet-like elastic members 112. The sheet-like elastic member 112 may be a synthetic rubber band, a stretchable nonwoven fabric, or a stretchable resin foam sheet.

FIG. 11(B) shows a sanitary napkin 501B, in which a second projection 215 is raised by a plurality of elastic members 212 to have a T-shaped cross section.

It should be appreciated that the second projection may have any other shape.

Figure 12:
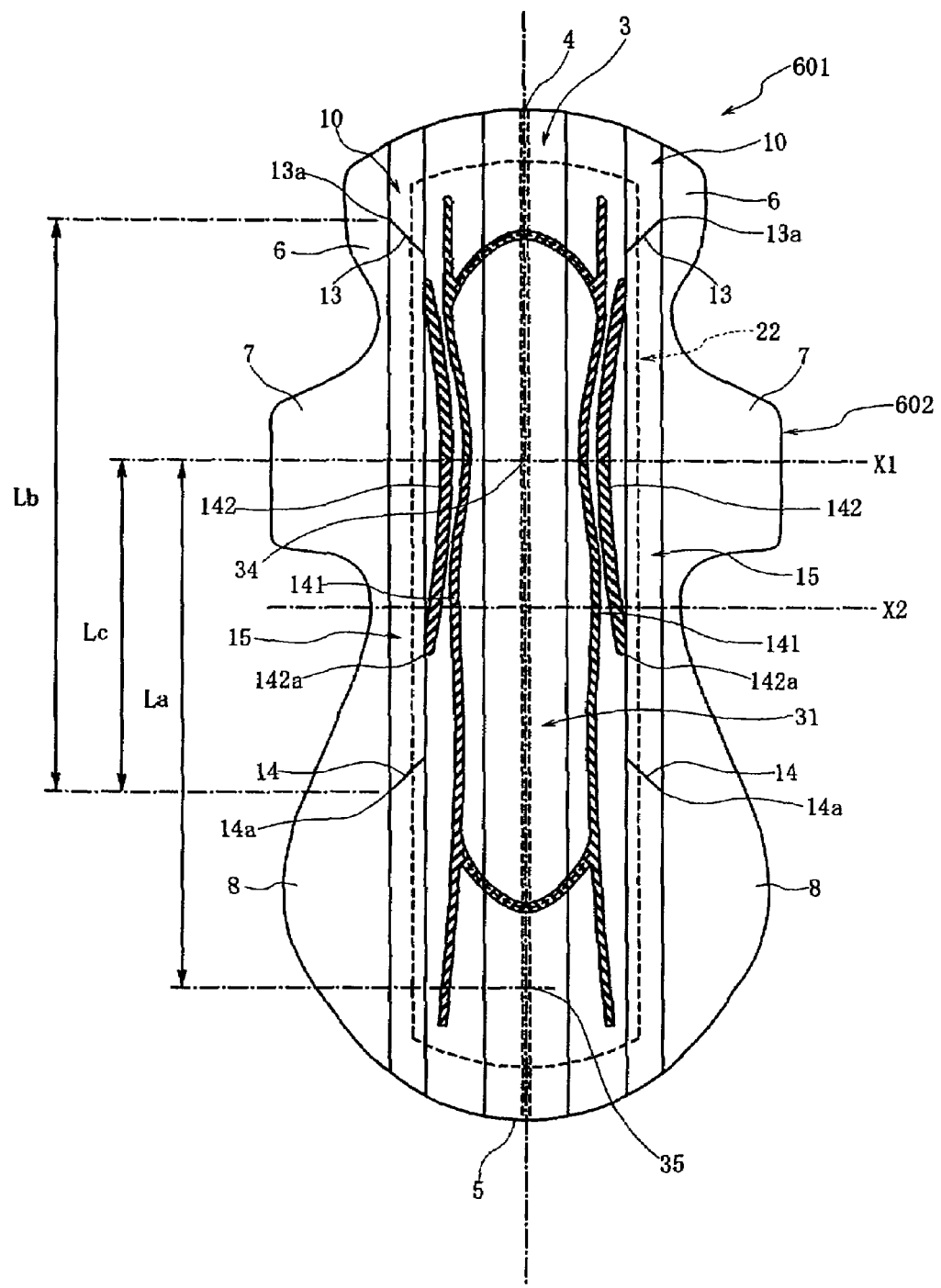
FIG. 12 is a plan view showing a body surface of a flattened sanitary napkin according to a sixth embodiment of the present invention.

FIG. 12 is a plan view corresponding to FIG. 2, in which a sanitary napkin 601 according to a sixth embodiment of the present invention is flattened.

The sanitary napkin 601 has a napkin body 602, on which the first surface element 3 provides the first projection 31 and the second surface elements 10 provide the second projections 15 in the same manner as in the first embodiment.

The napkin body 602 according to the sixth embodiment and the napkin body 2 according to the first embodiment differ only in the arrangement of compression lines on the body surface. In the napkin body 602 shown in FIG. 12, auxiliary compression lines 142, 142 are arranged laterally outside compression lines 141 which are arranged in the same way as the compression lines 41 shown in FIG. 2. The auxiliary compression line 142 extends longitudinally with center at the vaginal-facing reference line X1. More specifically, the auxiliary compression line 142 extends forward beyond the front end 34 of the first projection 31 with its rear end 142a located midway of the overlap region of the length Lc, in which the second projections 15 lie on laterally opposite sides of the first projection 31. In the embodiment shown in FIG. 12, the rear end 142a is located almost at the midpoint of the length Lc of the overlap region.

In the front region, which is subjected to the elastic contractive force of the second projections 15, the bending stiffness of the napkin body 602 is significantly increased by the compression lines 141 and the auxiliary compression lines 142. Thus, when curved, the front region tends to have a relatively large radius of curvature. In the overlap region, on the other hand, since the auxiliary compression lines 142 end almost at the midpoint of the length Lc, the napkin body 602 can easily be bent at the rear ends 142a of the auxiliary compression lines 142.

Therefore, the napkin body 602 can easily conform to the contours of the woman's crotch with a small radius of curvature on or slightly behind the anus-facing reference line X2.

Figure 13:
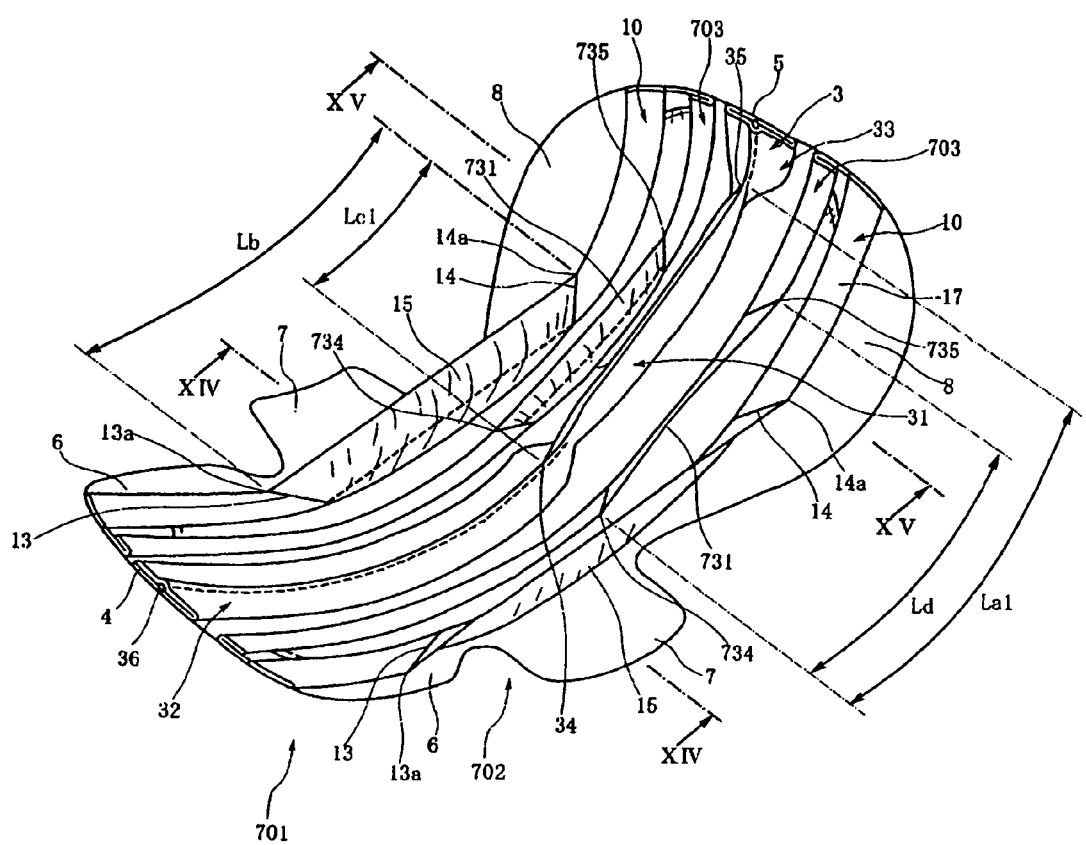
FIG. 13 is a perspective view of a sanitary napkin according to a seventh embodiment of the present invention in a natural state where no external force is exerted thereon.
Figure 14:
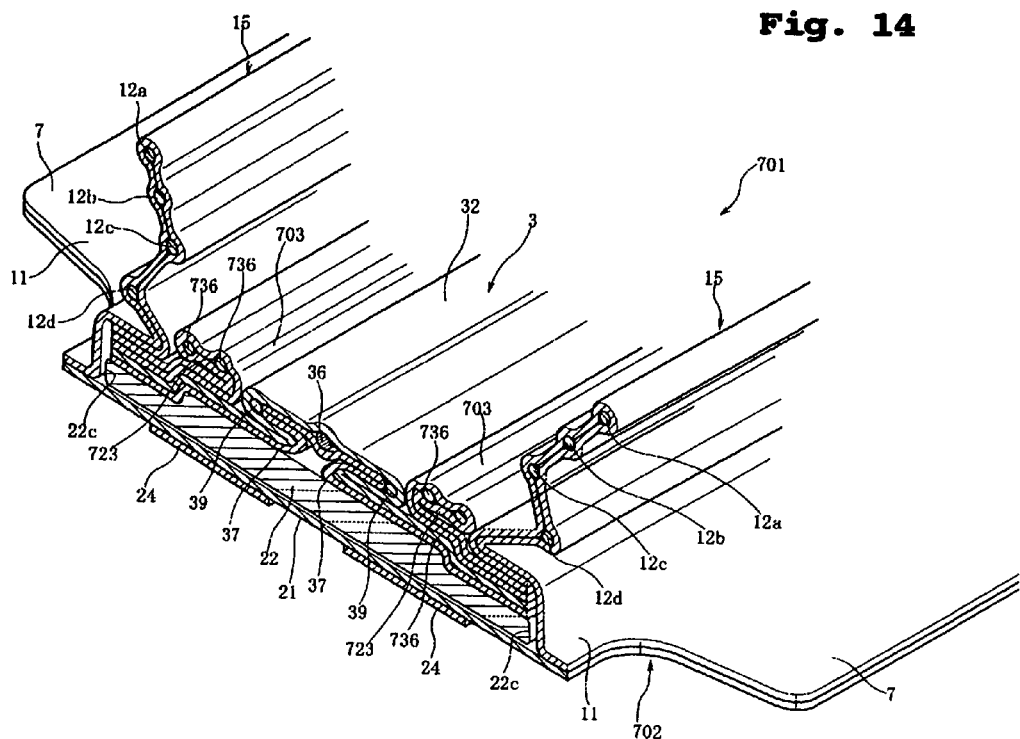
FIG. 14 is a sectional view taken along line XIV-XIV of FIG. 13.
Figure 15:
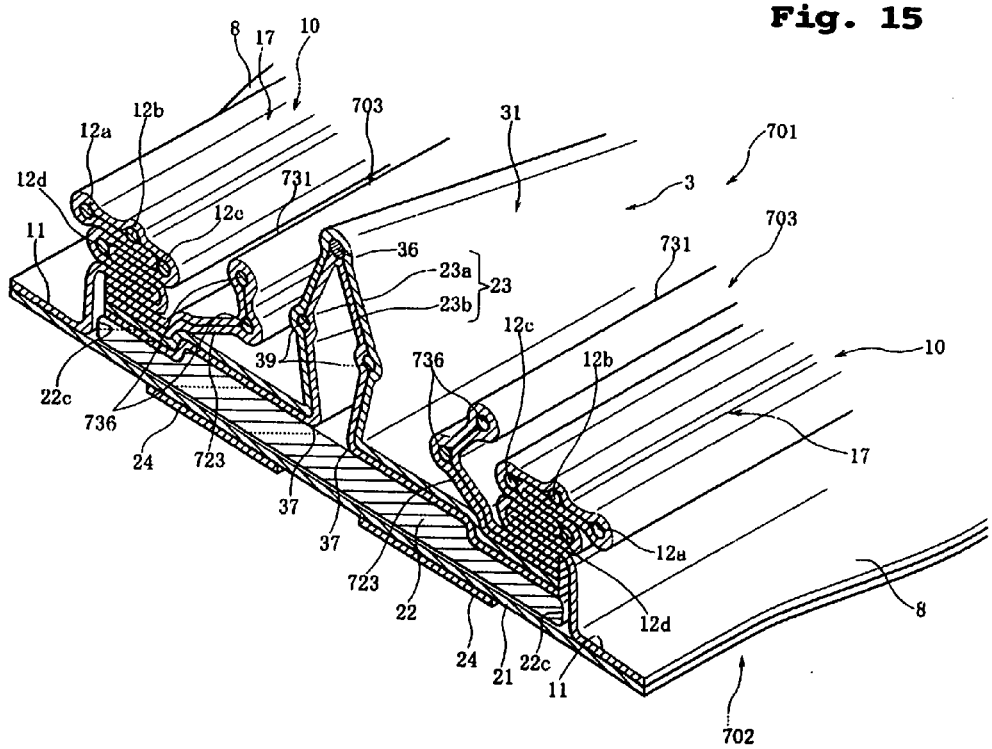
FIG. 15 is a sectional view taken along line XV-XV of FIG. 13.

FIG. 13 is a perspective view of a sanitary napkin 701 according to a seventh embodiment of the present invention in a natural state where no external force is exerted thereon, FIG. 14 is a sectional view taken along line XIV-XIV of FIG. 13, and FIG. 15 is a sectional view taken along line XV-XV of FIG. 13.

The sanitary napkin 701 has a napkin body 702 which is substantially the same as the napkin body 2 of the first embodiment.

The second surface elements 10 and the second projections 15 have the same shapes as those of the first embodiment. The second surface element 10 is constructed by bonding the elastic members 12a-12d in the side sheet 11. Between the front end 13a and the rear end 14a, the second surface element 10 is raised from the body surface of the napkin body 702 to provide the second projection 15, which serves as a leakage preventing wall. The second projection 15 has the length Lb.

The first surface element 3 and the first projection 31 also have almost the same shapes as those of the first embodiment. The first surface element 3 is constructed by the topsheet 23, the elastic member 36, and the pair of side elastic members 39. Between the front end 34 and the rear end 35, the first surface element 3 is raised from the body surface of the napkin body 702 to provide the first projection 31. The front flat portion 32 is provided forward of the front end 34, and the rear flat portion 33 is provided behind the rear end 35. In FIG. 13, the length of the first projection 31 is indicated by La1. The length La1 is slightly shorter than the length La of the first projection 31 shown in FIG. 2. In FIG. 13, the front end 34 is located slightly behind the vagina-facing reference line X1 and near the anus-facing reference line X2.

In the sanitary napkin 701 shown in FIG. 13, the length of the overlap region, where the second projections 15 lie on laterally opposite sides of the first projection 31, is indicated by Lc1. As set forth above, the length Lc1 is preferably equal to or greater than 15 mm, more preferably equal to or greater than 30 mm.

The sanitary napkin 701 further includes a pair of third surface elements 703 on the body surface of the napkin body 702. The third surface elements 703 lie on laterally opposite sides of the longitudinal centerline Oy and between the first surface element 3 and the second surface elements 10.

As shown in FIGS. 14 and 15, second topsheets 723 are disposed on the topsheet 23 and lie opposite one another on the body surface of the napkin body 702. The second topsheet 723 is hydrophilic and permeable to liquid and may be a laminate of first and second liquid-permeable sheets like the topsheet 23. In the third surface element 703, furthermore, a plurality of elastic members 736 are bonded between the first and second liquid-permeable sheets while being stretched longitudinally.

Between front and rear ends 734, 735, as shown in FIGS. 13 and 15, the third surface elements 703 are raised from the body surface of the napkin body 702 to provide a pair of third projections 731.

In FIG. 13, the length of the third projection 731 is indicated by Ld. The front ends 734 of the third projections 731 and the front end 34 of the first projection 31 lie approximately on the same straight line. As a result, the midpoint between the front and rear ends 734, 735 of the third projection 731 is located behind the midpoint between the front and rear ends 13a, 14a of the second projection 15. In the overlap region of the length Lc1, moreover, both the second projections 15 and the third projections 731 lie on laterally opposite sides of the first projection 31. In other words, all the first projection 31, the second projections 15, and the third projections 731 lie side-by-side in the overlap region of the length Lc1. Behind the rear ends 14a of the second projections 15, only the third projections 731 lie on laterally opposite sides of the first projection 31.

In the sanitary napkin 701, since all the first projection 31, the second projections 15, and the third projections 731 exert an elastic contractive force on the overlap region of the length Lc1, a high bending stress acts on the overlap region of the napkin body 702. Behind the rear ends 14a of the second projections 15, both the first projection 31 and the third projections 731 exert an elastic contractive force; forward of the front end 34 of the first projection 31, only the second projections exert an elastic contractive force.

Accordingly, the bending stress acting on napkin body 702 can easily be made different for different regions such that the overlap region>the rear region>the front region, and the napkin body 702 can easily conform to the contours of the woman's crotch shown in FIG. 6 with a small radius of curvature behind the anus-facing reference line X2.

Here, the front ends 734 of the third projections 731 are not necessarily required to lie on the same straight line as the front end 34 of the first projection 31, and may be located forward of or behind the front end 34 of the first projection 31. However, the length of the overlap region where all the first projection 31, the second projections 15, and the third projections 731 lie side-by-side is preferably equal to or more than 15 mm, more preferably equal to or more than 30 mm.

When the sanitary napkin 701 is worn, since the third projections 731 can be kept in contact with the surface of the buttocks on both sides of the first projection 31, which fits in the intergluteal cleft behind the anus, rearward leakage of menstrual blood during sleep can be effectively prevented.

Figure 16:
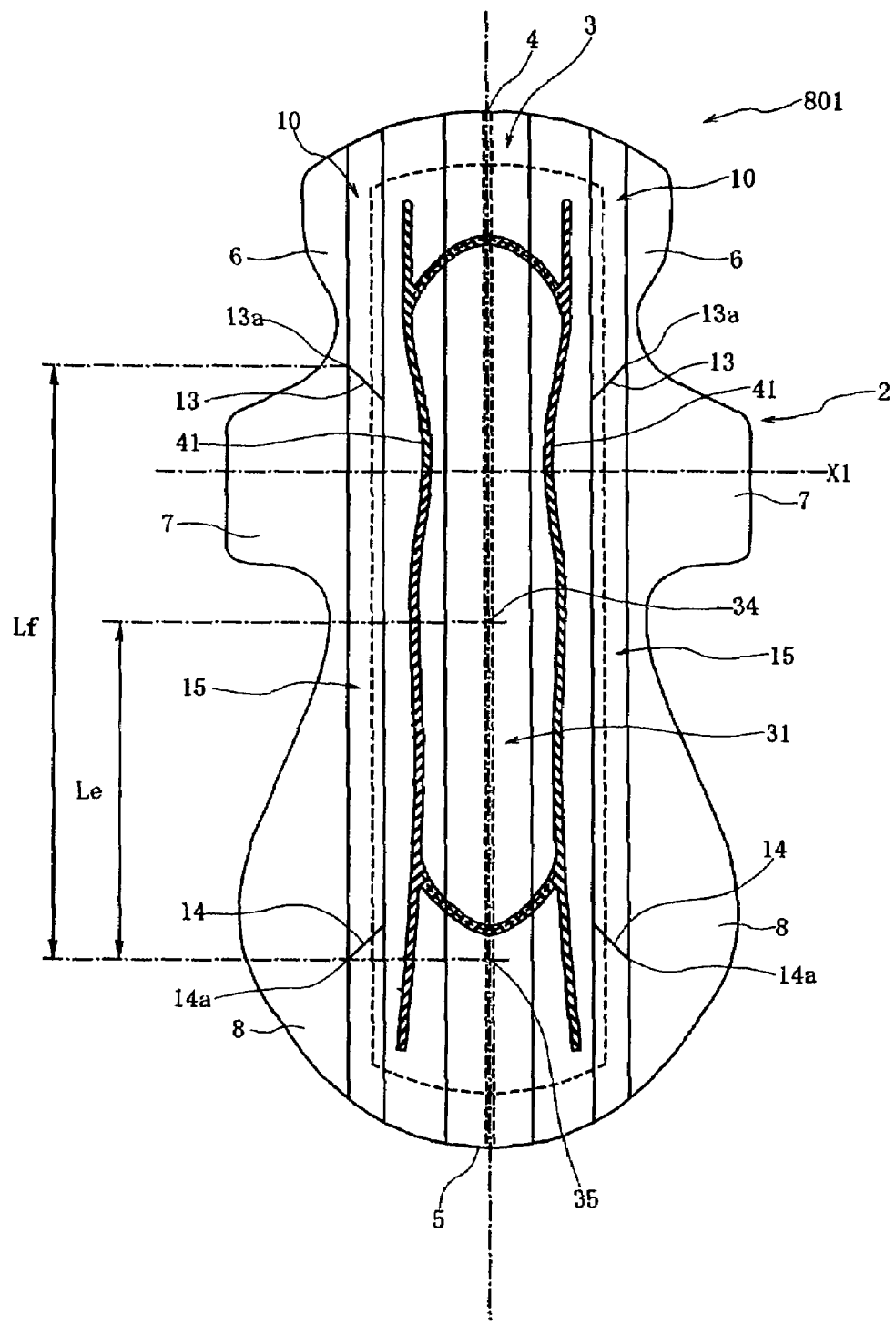
FIG. 16 is a plan view showing a body surface of a flattened sanitary napkin according to an eighth embodiment of the present invention.
Figure 17:
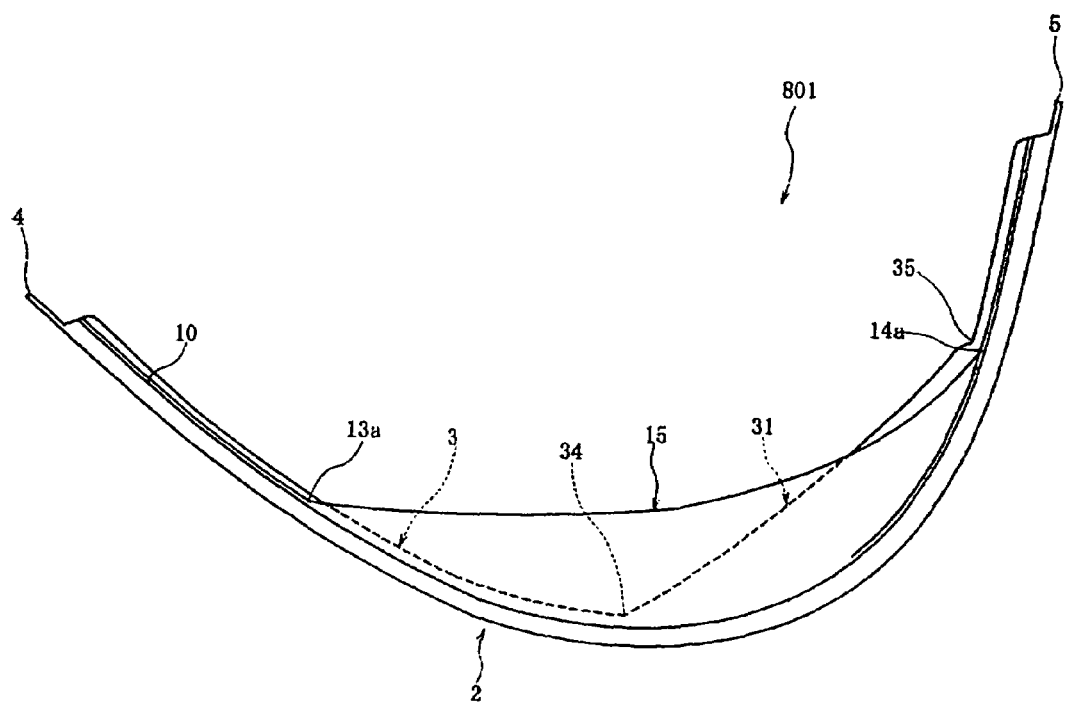
FIG. 17 is a side view of a sanitary napkin according to the eighth embodiment in a natural state where no external force is exerted thereon.

FIG. 16 is a plan view corresponding to FIG. 2, in which a sanitary napkin 801 according to an eighth embodiment of the present invention is flattened, and FIG. 17 is a side view of the sanitary napkin 801 in a natural state where no external force is exerted thereon.

In the sanitary napkin 801 according to the eighth embodiment, the napkin body 2 is substantially the same as that of the first embodiment. Moreover, the first surface element 3, the first projection 31, the second surface element 10, and the second projection 15 have the same basic constructions as those of the first embodiment. However, the first projection 31 and the second projection 15 are different in length from those of the first embodiment.

In the sanitary napkin 801, as shown in FIG. 16, the first projection 31 has a length Le which is slightly shorter than the length La of the first embodiment shown in FIG. 2, and the front end 34 is located on or near the anus-facing reference line X2. On the other hand, the second projection 15 has a length Lf which is slightly longer than the length Lb of the first embodiment, and the rear ends 14a are located approximately on the same straight line as the rear end 35 of the first projection 31.

Thus, the overlap region where the second projections 15 lie on laterally opposite sides of the first projection 31 has the same length Le as the first projection 31. In the front region forward of the front end 34 of the first projection 31, only the second projections 15 exert an elastic contractive force on the napkin body 2.

In the eighth embodiment, since the bending stress acting on the napkin body 2 is higher in the overlap region than in the front region, the sanitary napkin 801 tends to have a relatively large radius of curvature forward of the front end 34 and a relatively small radius of curvature between the front end 34 and the rear end 35, as shown in FIG. 17. The sanitary napkin 801, which is made deformable such that the radius of curvature is smaller in the rear than in the front, easily fits the woman's crotch shown in FIG. 6.

Figure 18:
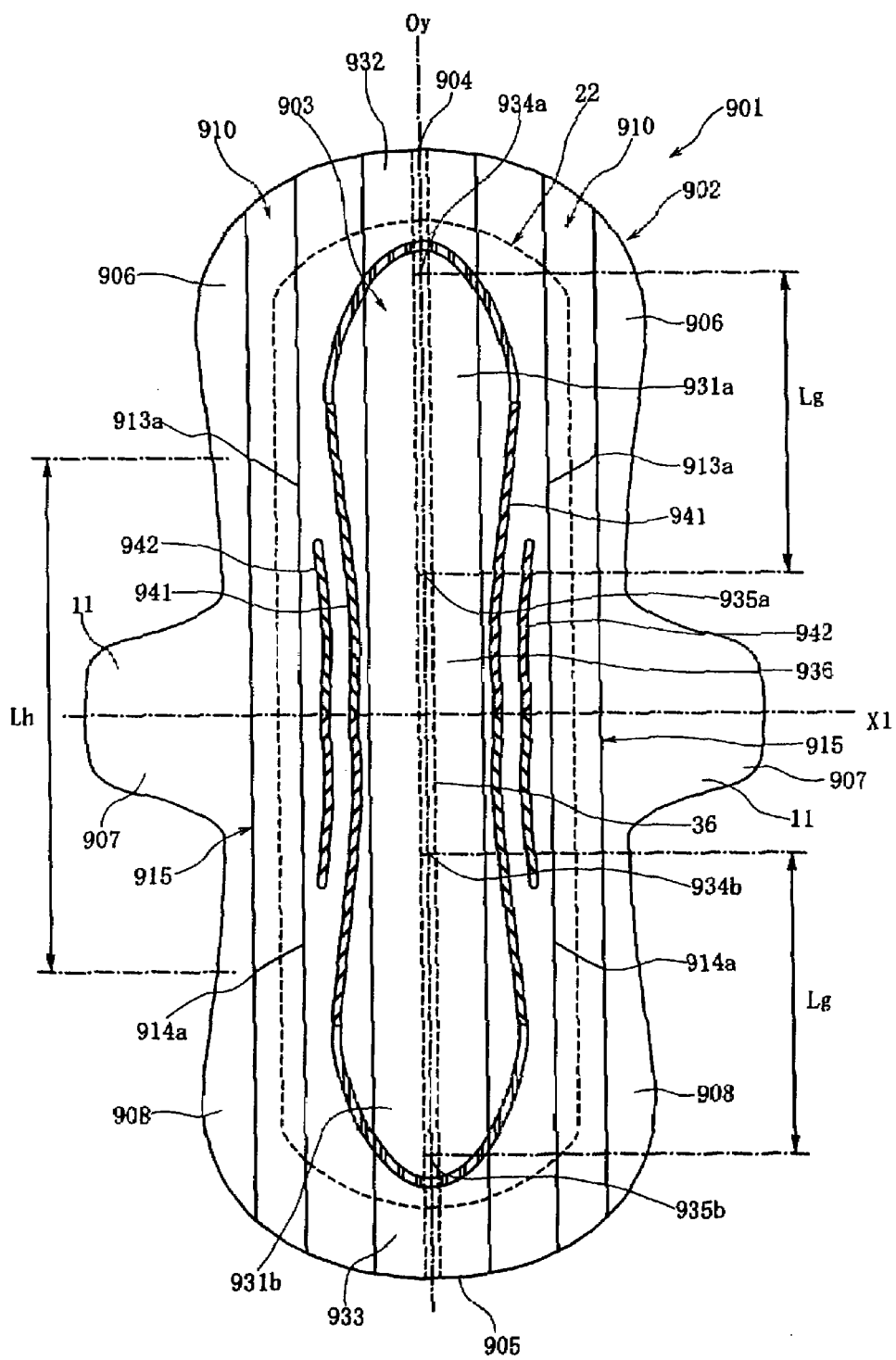
FIG. 18 is a plan view showing a body surface of a flattened sanitary napkin according to a ninth embodiment of the present invention.
Figure 19:
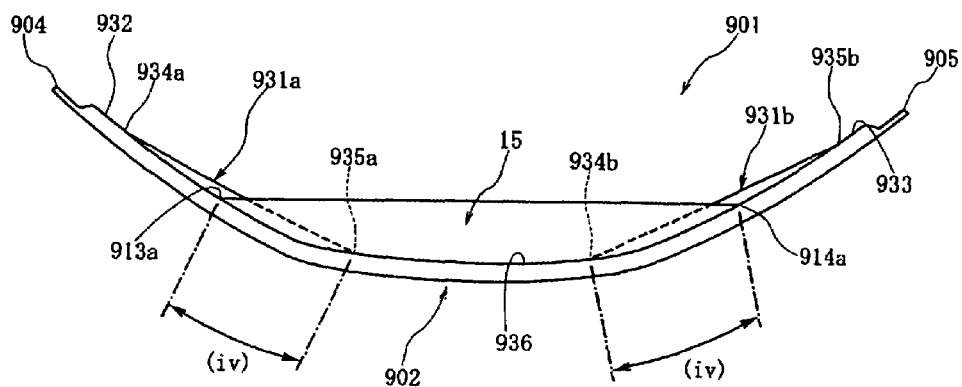
FIG. 19 is a side view of a sanitary napkin according to the ninth embodiment in a natural state where no external force is exerted thereon.

FIG. 18 is a plan view in which a sanitary napkin 901 according to a ninth embodiment of the present invention is flattened, and FIG. 19 is a side view of the sanitary napkin 901 in a natural state where no external force is exerted thereon.

In the sanitary napkin 901 according to the ninth embodiment, the napkin body 902 is constructed of the backsheet 21, the liquid-absorbent layer 22, the topsheet 23, and the side sheets 11 to have front flaps 906, fold-back flaps 907, and rear flaps 908.

The length of the napkin body 902 as measured between front and rear edges 904, 905 is shorter than the length L1 of the napkin body 2 according to the first embodiment shown in FIG. 2. The fold-back flaps 907 are located centrally of the length of the napkin body 902, and the vagina-facing reference line X1 longitudinally bisects the napkin body 902. The sanitary napkin 901 is adapted such that when the vagina-facing reference line X1 faces the center of the vaginal opening (b) shown in FIG. 6, the front edge 904 is located slightly forward of the pubis and the rear edge 905 is located near or slightly behind the location (a) slightly behind the anus 55.

On the body surface of the napkin body 902, the topsheet 23 provides a first surface element 903 which extends on the longitudinal centerline Oy. The first surface element 903 also includes the elastic member 36 and the side elastic members 39 in the same manner as shown in FIG. 3.

In the front part of the sanitary napkin 901, the first surface element 903 has a first front end 934a and a first rear end 935a, as shown in FIG. 18. Between the first front end 934a and the first rear end 935a, a first projection 931a exerts a longitudinal elastic contractive force to raise itself from the body surface of the napkin body 902, as shown in FIG. 19. In the rear part of the sanitary napkin 901, on the other hand, the first surface element 903 has a second front end 934b and a second rear end 935b. Between the second front end 934b and the second rear end 935b, another first projection 931b exerts a longitudinal elastic contractive force to raise itself from the body surface of the napkin body 902, as shown in FIG. 19.

The first rear end 935a and the second front end 934b are spaced an equal distance longitudinally from the vagina-facing reference line X1. Between the first rear end 935a and the second front end 934b, the first surface element 903 is folded flat to provide a central flat portion 936. Forward of the first front end 934a and behind the second rear end 935b, there are provided a front flat portion 932 and a rear flat portion 933, respectively.

On the body surface of the napkin body 902, second surface elements 910 lie opposite one another. The second surface element 910 is constructed of the side sheet 11 and the elastic members 12a-12d, like the second surface element 10 shown in FIGS. 3 and 4. Between front and rear ends 913a, 914a, each second surface element 910 is raised from the body surface of the napkin body 902 to provide a second projection 915 which has the same construction as the second projection 15 shown in FIG. 3. The front and rear ends 913a, 914a of the second projection 915 are spaced an equal distance longitudinally from the vagina-facing reference line X1.

The first projection 931a in the front part and the first projection 931b in the rear part have an equal length Lg and the second projection 915 has a length Lh. Thus, the napkin body 902 has front and rear overlap regions. In the front overlap region, front parts of the second projections 915 lie on laterally opposite sides of a rear part of the first projection 931a. In the rear overlap region, rear parts of the second projections 915 lie on laterally opposite sides of a front part of the first projection 931b. In FIG. 19, the individual overlap regions are indicated by (iv). The length of the overlap region (iv) is preferably equal to or greater than 15 mm, more preferably equal to or greater than 30 mm.

As shown in FIG. 19, since the overlap regions (iv) are spaced longitudinally from the vagina-facing reference line X1, the bending stress acting on the napkin body 902 is relatively low in the central region inclusive of the vagina-facing reference line X1 and relatively high in the overlap regions (iv). When the napkin body 902 is curved, therefore, the radius of curvature tends to be relatively large in the central region, which is intended to face the vagina, and relatively small in the front and rear overlap regions (iv). Thus, the central region easily fits on the vagina and the overlap regions (iv) easily fit on the pubis forward of the vagina and the sharply curved region behind the anus.

Moreover, since both compression lines 941 and auxiliary compression lines 942 are formed in the central region defined between the first rear end 935a and the second front end 934b, as shown in FIG. 18, the central region resists bending to maintain a relatively large radius of curvature.

Figure 20:
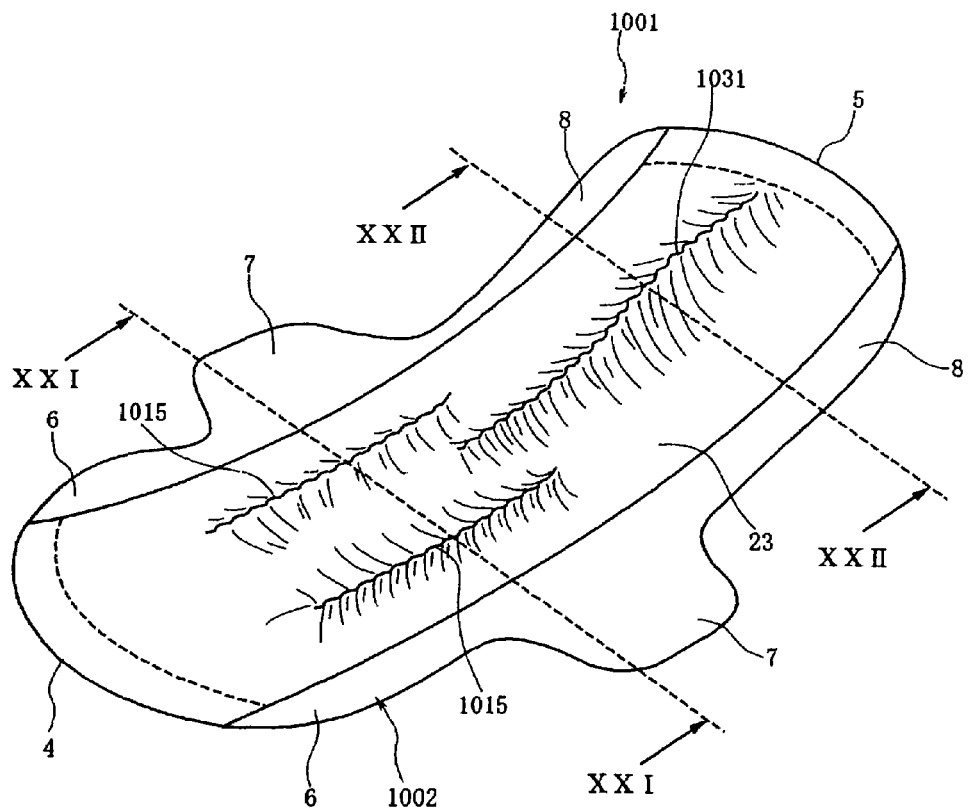
FIG. 20 is a perspective view of a sanitary napkin according to a tenth embodiment of the present invention in a natural state where no external force is exerted thereon.
Figure 21:
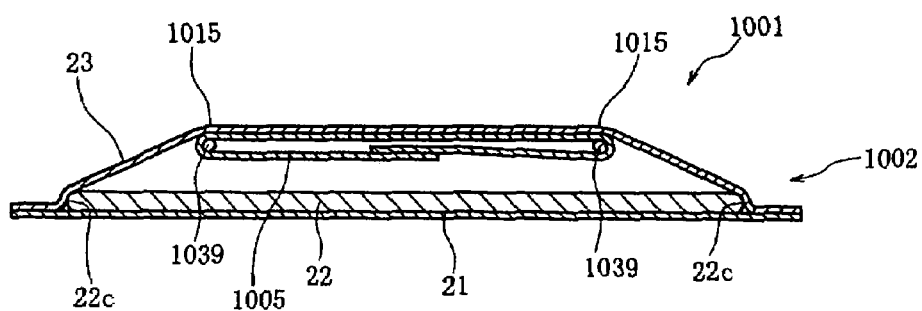
FIG. 21 is a sectional view taken along line XXI-XXI of FIG. 20.
Figure 22:
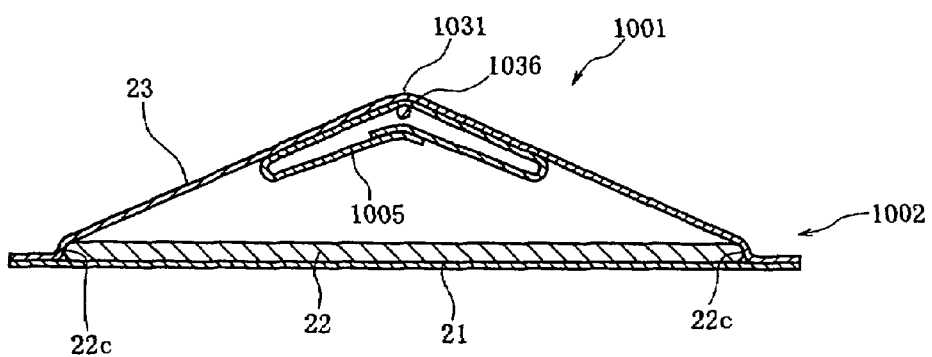
FIG. 22 is a sectional view taken along line XXII-XXII of FIG. 20.

FIG. 20 is a perspective view of a sanitary napkin 1001 according to a tenth embodiment of the present invention in a natural state where no external force is exerted thereon, FIG. 21 is a sectional view taken along line XXI-XXI of FIG. 20, and FIG. 22 is a sectional view taken along line XXII-XXII of FIG. 20.

As shown in FIGS. 21 and 22, the sanitary napkin 1001 has a napkin body 1002 constructed of the backsheet 21, the liquid-absorbent layer 22, and the topsheet 23. At the front and rear edges 4, 5, the topsheet 23 is bonded to the body surface of the liquid-absorbent layer 22. Aside from the front and rear edges 4, 5, the topsheet 23 is bonded to the side edges 22c, 22c of the liquid-absorbent layer 22 and the backsheet 21 outside the side edges 22c, 22c, but remains unbonded to the body surface of the liquid-absorbent layer 22. Thus, the topsheet 23 is allowed to move away from the body surface of the liquid-absorbent layer 22, as shown in FIGS. 21 and 22.

In the front part of the sanitary napkin 1001, side elastic members 1039, 1039 are arranged to extend a given length in the longitudinal direction, as shown in FIG. 21. The side elastic members 1039, 1039, which are laterally spaced from each other, are adapted to exert a longitudinal elastic contractive force between front and rear connection points to move away from the body surface of the liquid-absorbent layer 22. Thus, second projections 1015, 1015 are formed with the side elastic members 1039, 1039 at their apexes.

In the rear part of the sanitary napkin 1001, a central elastic member 1036 is arranged to extend on a longitudinal centerline. The central elastic member 1036 is adapted to exert a longitudinal elastic contractive force between front and rear connection points to move away from the body surface of the liquid-absorbent layer 22.

Thus, a first projection 1031 is formed in the rear part of the sanitary napkin 1001 with the central elastic member 1036 at its apex.

Behind the vagina-facing reference line (not shown), the second projections 1015, 1015 lie on laterally opposite sides of the first projection 1031 to provide an overlap region, as shown in FIG. 20.

As shown in FIGS. 21 and 22, a reinforcing sheet 1005 is disposed on the garment surface of the topsheet 23 to cover both the central elastic member 1036 and the side elastic members 1039. The reinforcing sheet 1005 may be stiff and made of a hydrophilic or liquid-permeable material, such as an air-laid pulp, an apertured resin film, a paper material, or a through-air bonded nonwoven fabric.

With the reinforcing sheet 1005, the topsheet 23 can easily be kept flat between the second projections 1015, 1015 in the front part of the sanitary napkin 1001, as shown in FIG. 21. In the rear part, on the other hand, two slopes of the first projection 1031 can easily be kept flat, as shown in FIG. 22.

The sanitary napkin 1001 also has front and rear regions. The front region is located forward of the overlap region and has the rest of the second projections 1015, 1015, and the rear region is located behind the overlap region and has the rest of the first projection 1031. Here, the bending stress acting on the napkin body 1002 may be made different for different regions such that the overlap region>the rear region>the front region.

In the foregoing embodiments, although it has been described that the bending stress acting on the napkin body preferably varies such that the overlap region>the rear region>the front region, the bending stress may vary such that the overlap region>the rear region=the front region, or the overlap region>the front region>the rear region.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but should be understood to include all possible embodiments which can be embodied within a scope encompassed and equivalent thereof with respect to the feature set out in the appended claims.

What is claimed is:

1. A sanitary napkin comprising:
a napkin body having a liquid-absorbent layer for absorbing and retaining liquid; and
a first projection and a second projection, each of the projections extending in a longitudinal direction and each comprising an elastic member for exerting an elastic contractive force between longitudinally opposing front and rear ends to concavely curve the body surface of the napkin body and raise itself from the body surface of the napkin body, wherein:
the first projection is formed with a top sheet and a tube-like shaped surface material which extends longitudinally and exerts an elastic contractive force between the front and rear ends to form the projection,
the napkin body has an overlap region where a portion of the second projection extending forward from the rear end of the second projection lies laterally opposite to a portion of the first projection extending rearward from the front end of the first projection, and wherein a portion of the second projection extending rearward from the front end of the second projection and a portion of the first projection extending forward from the rear end of the first projection each lie outside of the overlap region,
the napkin body has front and rear regions on longitudinally opposite sides of the overlap region; front and rear ends of the front region are defined by the front end of the second projection and the front end of the first projection, respectively; front and rear ends of the rear region are defined by the rear end of the second projection and the rear end of the first projection, respectively,
wherein the napkin body has compression lines which extend longitudinally at least in the front region, and
the napkin body further comprises a third projection which also exerts an elastic contractive force between longitudinally opposing front and rear ends to concavely curve the body surface of the napkin body, wherein a midpoint between the front and rear ends of the first projection and a midpoint between the front and rear ends of the third projection are each located behind a midpoint between the front and rear ends of the second projection.

2. The sanitary napkin of claim 1, wherein the first projection extends on a longitudinal centerline of the napkin body, and multiple second projections lie on laterally opposite sides of the longitudinal centerline.

3. The sanitary napkin of claim 1, wherein the first and second projections are each comprised of a sheet allowed to rise from the body surface of the napkin body and an elastic member adapted to exert an elastic contractive force between the front and rear ends for raising the sheet.

4. The sanitary napkin of claim 1, wherein the midpoint between the front and rear ends of the first projection is located behind the midpoint between the front and rear ends of the third projection.

5. The sanitary napkin of claim 1, wherein the front and rear ends of the first projection are located behind the front and rear ends of the second projection, respectively.

6. The sanitary napkin of claim 5, wherein a bending stress which is exerted on the napkin body by the first and second projections is higher in the overlap region than in the front and rear regions.

7. The sanitary napkin of claim 6, wherein the bending stress in the front region is equal to or lower than the bending stress in the rear region.

8. The sanitary napkin of claim 1, wherein a midpoint between front and rear ends of the overlap region is located behind a vagina-facing reference line of the napkin body.

9. The sanitary napkin of claim 8, wherein the front end of the first projection is not spaced more than 120 mm rearward from the vagina-facing reference line.

10. The sanitary napkin of claim 1, wherein in the overlap region, third projections lie on laterally opposite sides of the first projection.

11. The sanitary napkin of claim 10, wherein the third projections are located between the first projection and the second projection.

* * * * *